United States Patent [19]

Haugen

[11] Patent Number: 5,369,484
[45] Date of Patent: Nov. 29, 1994

[54] MULTIPLE DISCRETE ANALYZER TEST APPARATUS AND METHOD

[75] Inventor: Douglas G. Haugen, Durham, N.C.

[73] Assignee: Akzo N.V., Arnhem, Netherlands

[21] Appl. No.: 973,956

[22] Filed: Nov. 9, 1992

[51] Int. Cl.⁵ .............................................. G01J 3/02
[52] U.S. Cl. ...................... 356/326; 356/328; 364/498; 364/571.02
[58] Field of Search ............... 356/328, 326, 319, 320, 356/323, 325, 326, 328; 364/498, 526, 571.02

[56] References Cited

U.S. PATENT DOCUMENTS

| | | | |
|---|---|---|---|
| 4,323,309 | 4/1982 | Akitomo et al. | 356/319 |
| 4,399,502 | 8/1983 | MacDonald et al. | 364/189 |
| 4,703,437 | 10/1987 | Nishimura | 356/319 |
| 4,930,891 | 6/1990 | Sato | 356/326 |
| 4,935,875 | 6/1990 | Shah et al. | 356/300 |
| 5,002,392 | 3/1991 | Swope . | |
| 5,030,005 | 7/1991 | Swope et al. | 356/243 |
| 5,116,122 | 5/1992 | Fukuma | 356/326 |
| 5,125,748 | 6/1992 | Bjornson et al. | 356/414 |
| 5,245,176 | 9/1993 | Haugen | 250/208.3 |

*Primary Examiner*—F. L. Evans
*Assistant Examiner*—Peter J. Rashid
*Attorney, Agent, or Firm*—Spencer, Frank & Schneider

[57] ABSTRACT

A computer based system for testing an optical monitoring system includes a program having program instruction and optical monitoring system parameters, for implementing a plurality of tests of an optical monitoring system. A computer includes at least one processor for executing the program instructions, storage components for storing program instructions and test data, including the optical system parameters, a user input for inputting commands, and a display for displaying a menu of available test commands, test results and other data. An interface is provided for interfacing the optical monitoring system to tile computer for exchange of control and data signals. A fixture is provided for mounting the optical monitoring system during testing.

29 Claims, 25 Drawing Sheets

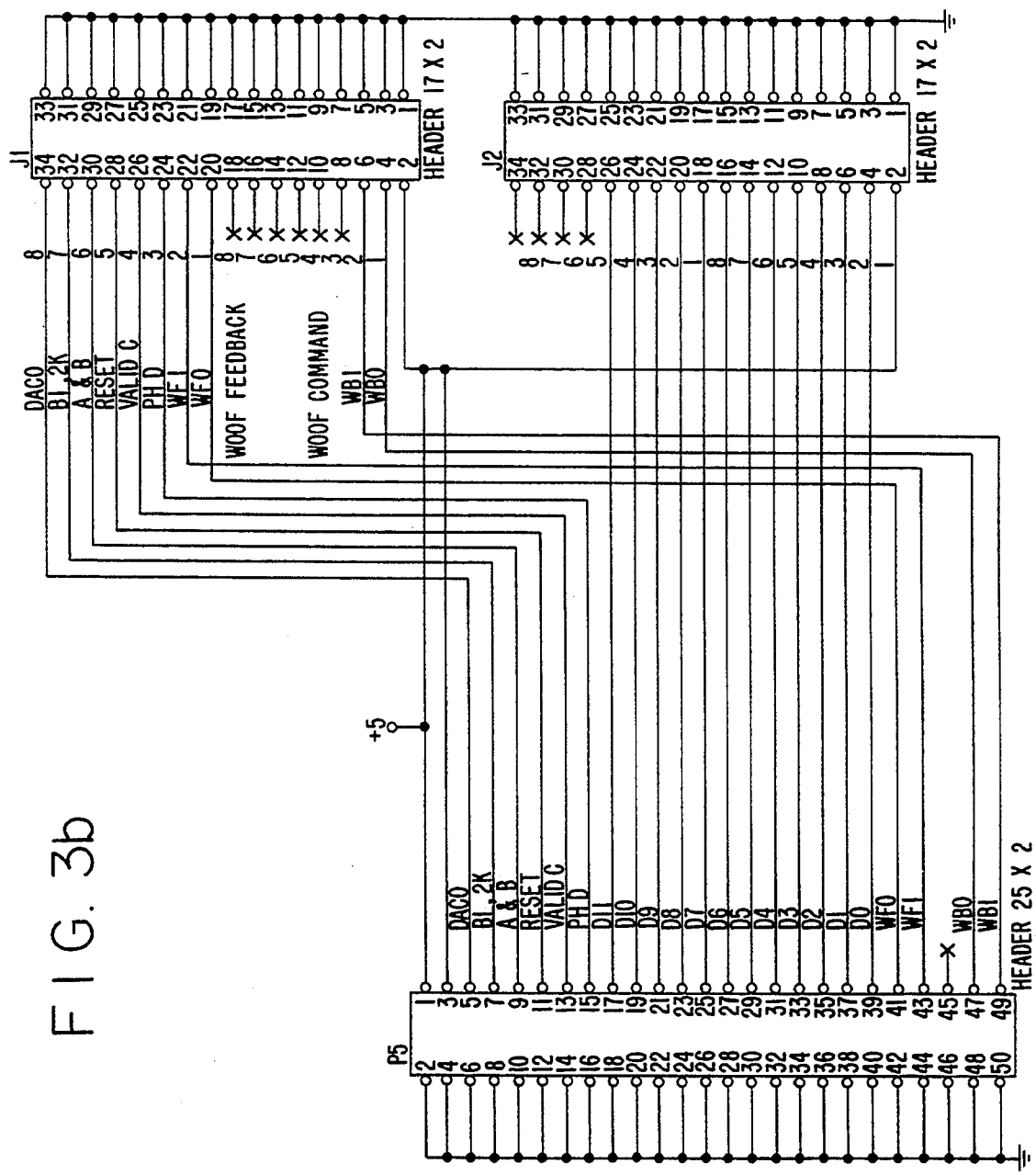
FIG. 3b
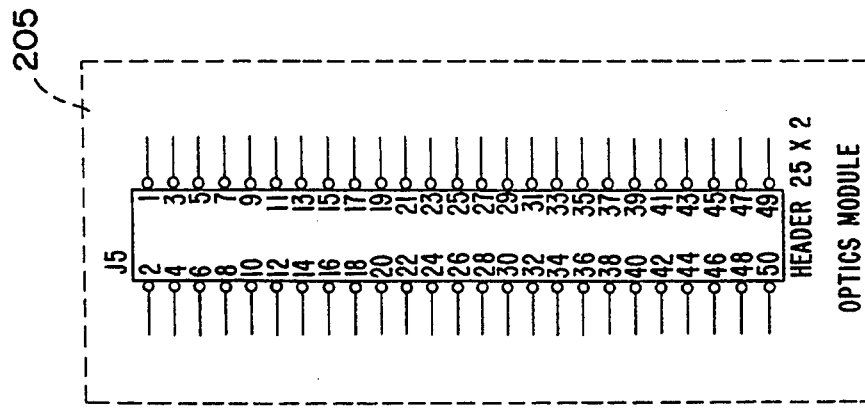

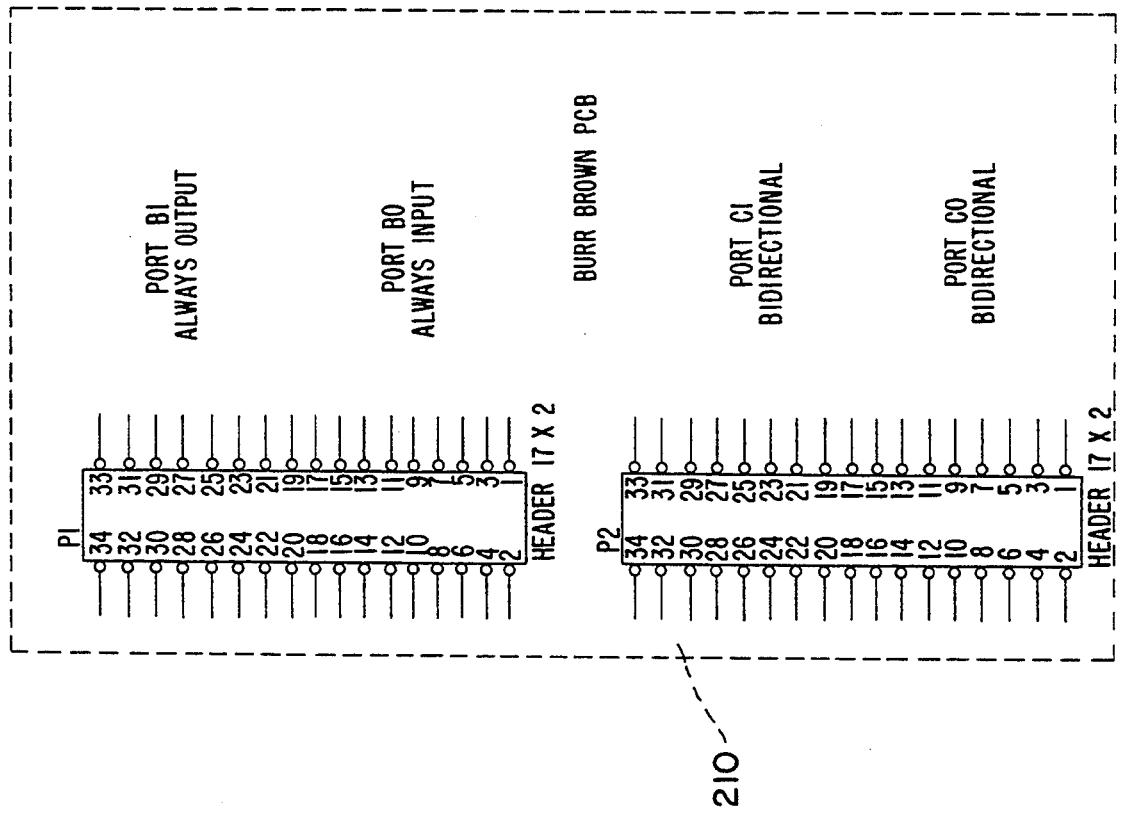

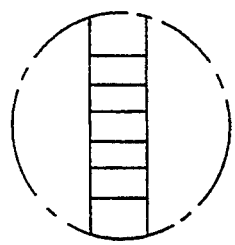
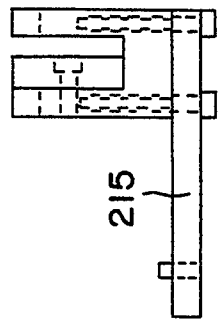
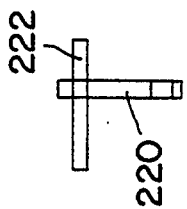
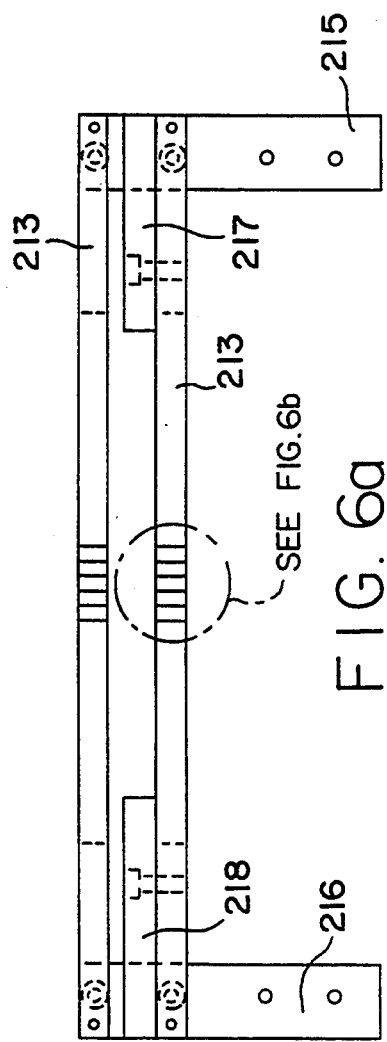
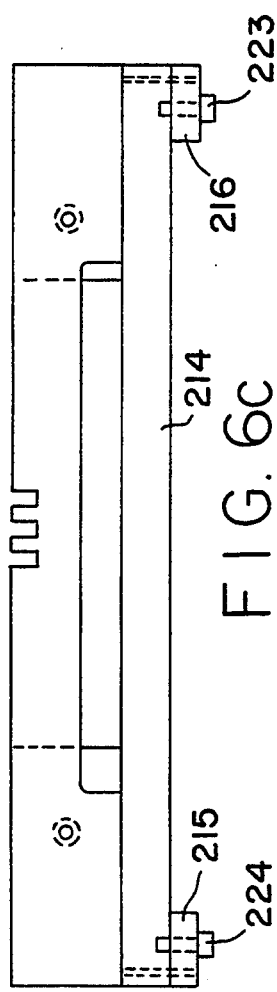
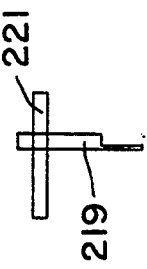

MULTIPLE DISCRETE ANALYZER TEST APPARATUS AND METHOD

CROSS REFERENCE TO RELATED APPLICATIONS

This application is related to the copending U.S. patent application Ser. No. 07/896,579, titled "METHOD FOR SCANNING PHOTODIODES" filed Jun. 10, 1992, now U.S. Pat. No. 5,245,176, by Douglas G. Haugen, assigned to the same assignee as the present application, which is hereby incorporated by reference.

BACKGROUND OF THE INVENTION

1. Field of the Invention

The invention relates to the field of automating testing of complex equipment including electrical and optical components, and in particular to an apparatus and method for testing a multiple discrete analyzer (MDA) optical module.

2. Background Information

A multiple discrete analyzer, referred to hereafter as an MDA, is a complex machine for automatically performing multiple coagulation related diagnostic tests on human blood. An example of such a machine is described in U.S. Pat. No. 5,002,392, assigned to the assignee of the present application, hereby incorporated by reference.

Briefly, the MDA includes a multi-channel optical monitoring system for monitoring the spectral transmission of a plurality of blood samples. A plurality of light beams are generated and a plurality of optical monitoring stations (positions) are arranged along a pathway. Each station has an optical path formed by one of the light beams transverse to the pathway. The optical characteristics are monitored along the optical path at each station. A drive mechanism moves a plurality of reaction wells, each containing a reaction volume (blood sample), along the pathway from station to station. The respective reaction volumes dwell periodically at each station in each respective optical path transmitting a respective one of the light beams. A diffraction grating is provided for diffracting the beams transmitted by respective ones of the reaction volumes. The diffracted beams are focussed and at least one array of photodetectors is positioned for receiving the diffracted and focussed beams for producing electrical signals representing the spectral content of the diffracted beams. An electronic circuit detects the electrical signals of the array which may be stored for further processing and evaluation.

The multi-channel optical monitoring system includes a plurality of photodiode arrays illuminated by light beams projected onto the arrays by way of a shutter mechanism. Each of the light beams constitutes an optical channel and passes through a reaction well of a cuvette and then through a transmitting diffraction grating for the purpose of performing an optical analysis of a reaction volume, the blood sample, in the reaction well. The photodiode arrays each develop electrical signals corresponding to the spectral distribution of the respective beams falling on the arrays, and the arrays are periodically read by electronic scanning circuitry.

The disclosed shutter mechanism comprises a rotating shutter which includes a number of cam elements mounted on a motor driven shaft. The light beams are incident on the cams in a direction parallel to the rotational planes of the cams. Each cam element is aligned in a respective one of the optical channels and has a cut-out segment greater than 180° so that each cam will block the light beam that it is aligned with for a certain portion of the rotation and will pass the beam for a remaining portion of the rotation. The cut-out segments of the cams are angularly arranged relative to one another so that the rotating shutter sequentially passes the beams in a predetermined sequence.

Each cam thus constitutes a shutter element which opens and closes an optical path during each revolution. Actually, each revolution of a cam may be divided into four periods. A first period occurs during a portion of a turn when the cam completely blocks the optical path of the light beam. A second period occurs when an edge of the cam bordering on the cut-out segment passes through the optical path of the beam during which the optical beam is partially transmitted onto the photodiode array. This is the opening transition. A third period occurs at the conclusion of the opening transition when the cut-out segment of the cam is positioned so that the optical path of the beam is uninterrupted by the cam and therefore the entire beam is fully projected onto the photodiode array. The fourth period is the closing transition period when the other edge of the cut-out segment passes through the optical path of the beam so that the optical beam is again only partially transmitted onto the photodiode array. At the conclusion of the closing transition period the optical beam is totally blocked so that the optical channel enters into a dark period (the first period described above) until the next opening transition period.

The electronic scanning circuitry disclosed in U.S. Pat. No. 5,002,392 involves a charge storage mode of operation whereby each photodiode element integrates light projected thereon by virtue of an electron depletion of its p-n junction which is replenished at the time of scanning. The amount of charge required to replenish the electron depletion is a measure of the integrated light. The charge coupled mode of operation for electronically scanning a photodiode array is well known as disclosed in U.S. Pat. No. 5,002,392 and the prior art cited therein.

The charge storage mode of operation for scanning the photodiode arrays is desirable in an environment in which there are hundreds of low level optical signals that must be evaluated at high speeds and is economical in terms of cost and space since only a single charge coupled amplifier is required in lieu of a separate amplifier for each photodiode element.

Electronic control, interfacing and processing circuitry is associated with the above optical module components. The circuitry includes shutter rotation control circuitry, filter selection control circuitry, photodetector scanning and control circuitry, photodetector signal amplification circuitry, digital to analog and analog to digital convertor devices and other interface circuitry.

The above optical, electronic, and optoelectrical elements comprise the optical module of the MDA. The optical module is the critical element of the MDA and proper operation of the MDA is dependent on proper alignment and operation of the optical module. In the past, testing and alignment of the completed optical module has represented an insurmountable task given the large number of variables affecting its operation. Tests and adjustments had to be made during assembly of each portion of the module, resulting in increased manufacturing time and costs.

Testing and alignment of the completed optical module should ideally include testing and adjusting the sensing and control electronics, testing for light leakage, wavelength registration and testing, optical uniformity stability and alignment, and filter testing.

A need has, therefore, existed for an efficient, accurate and automatic way to test the completed MDA optical module as it leaves the manufacturer, arrives at a test facility and is installed in an MDA device.

SUMMARY OF THE INVENTION

It is an object of the present invention to provide an apparatus and method for testing the optical module of an MDA device, in particular, for performing alignment and diagnostic tests of the optical module.

According to one embodiment of the invention, an automated acceptance test procedure includes alignment, diagnostic and qualification tests. The alignment and diagnostic tests include displaying of all the elements of any of the arrays for a respective optical monitoring station, displaying of any single element of the arrays for all stations, and wavelength registration. Qualification testing provides traceability through the module's serial number stamped on the module and stored in a disk file.

Other test features include electrical systems tests, optical dark tests, wavelength tests, optical signal tests, and filter testing.

In addition to the above, mechanical compatibility of the optical module with a test fixture may be confirmed as a prerequisite to performing any of the automated tests. It is also advantageous to store test results to disk for later analysis.

According to an embodiment of the invention, a computer based method for testing an optical monitoring system which is electrically connected to a computer for exchanging control and data signals therewith, the computer having input means for selecting test commands and display means for displaying screens of information to a user, comprises displaying on the display means at least one screen showing a plurality of user selectable commands; and performing programmed tests with the computer on the optical monitoring system based on user selected commands input with the input means.

In a further embodiment of the computer based method, wherein the optical monitoring system includes optical components and electrical circuitry which may be disposed in a cabinet, a light source, a light modifying wheel, a shutter, and a plurality of photodiode arrays having elements, disposed at respective stations for receiving light from a respective plurality of optical channels, and wherein the plurality of user selectable commands include a display command, an electrical systems test command, an optical dark test command, a beam alignment test command, a wavelength registration test command, a profile test command, and a filter test command, the method further comprises performing preliminary testing while monitoring the output of the optical monitoring system, the preliminary testing including commanding the optical monitoring system to rotate a light modifying wheel associated therewith to ensure the wheel is responsive, and monitoring the optical monitoring system to check the operation of a shutter associated therewith by checking pulses associated therewith; upon selection of a display command, monitoring with the computer output signals from the optical monitoring system, displaying a screen representing photodiode array output on the computer display means, and selectively varying at least the array represented by the screen, the elements of the arrays represented by the screen, and the gain associated with an array element; upon selection of an electrical systems test command, monitoring the output of the optical monitoring system while selectively performing at least an electrical dark test to check the levels of dark current and noise associated with the electrical circuitry of the system, a digital bit test to check for stuck bits, i.e., that all bits change state, "toggle," at least once on command, in associated digital electrical circuitry of the system, a shutter speed test to check the rotational speed of the shutter, and a complete light modifying wheel test to test the accuracy of the light modifying wheel; upon selection of an optical dark test command, monitoring the output of the optical monitoring system to check the amount of ambient light leaking into the optical monitoring system through a cabinet associated therewith; upon selection of a beam alignment test command, monitoring the output of the optical monitoring system to check for cross-talk between optical channels of the optical monitoring system and for proper beam height; upon selection of a wavelength registration test command, monitoring the output of the optical monitoring system to determine the wavelength mid-frequency and bandwidth of each photodiode array element; upon selection of a profile test command, monitoring the output of the optical monitoring system to measure the amount of light reaching the photodetectors for each optical channel under normal operating conditions; and upon selection of a filter test command, monitoring the output of the optical monitoring system when different filters are used to test for proper operation.

In another embodiment of the computer based method, wherein the plurality of user selectable commands includes an all tests command, the method further comprises upon selection of the all tests command, after performing the preliminary testing, performing the electrical systems test command, the optical dark test command, the beam alignment test command, the wavelength registration test command, the profile test command, and the filter test command automatically. In another embodiment of the computer based method, the filter test command tests the optical monitoring system with at least a BG36 filter and a liquid crystal clot simulator used.

Test result data is advantageously stored to disk for trending analysis. For example, minimum, maximum, average and standard deviation data can be stored for the photodiode arrays for a series of optical modules tested. This data can be subjected to statistical analysis to determine if any trends are apparent, for example, for the last one hundred modules tested.

In another embodiment of the computer based method, wherein each optical monitoring system has a unique serial number associated therewith, the method further comprises confirming the programmed tests are suitable for use with the optical monitoring system prior to their execution.

In an embodiment of a system for testing an optical module of an analytical device having optical components and electrical circuitry, the system comprises program means comprising program instruction and optical module parameters, for implementing a plurality of tests of at least one optical module; programmable means comprising a data processing system having processor means for executing the program instructions, memory means for storing program instructions and test data including optical module parameters, user input means for inputting commands, and display means for displaying screens of information to a user including a menu of available test commands, test results and other data; interface means for interfacing the optical module to the programmable means to facilitate exchange of control and data signals therewith; and fixture means for mounting the optical module during testing. The fixture means, besides providing a structure on which to mount the optical module, enables testing of beam alignment and cross-talk. The fixture means simulates actual operational mounting on an MDA device.

Other objects, features and advantages of the invention will become apparent from the following detailed description taken in conjunction with the drawings, and appended claims.

BRIEF DESCRIPTION OF THE DRAWINGS

FIGS. 6a to 6f show the assembly of the parts of FIGS. 5.

DETAILED DESCRIPTION OF THE PREFERRED EMBODIMENT

Figure 1:
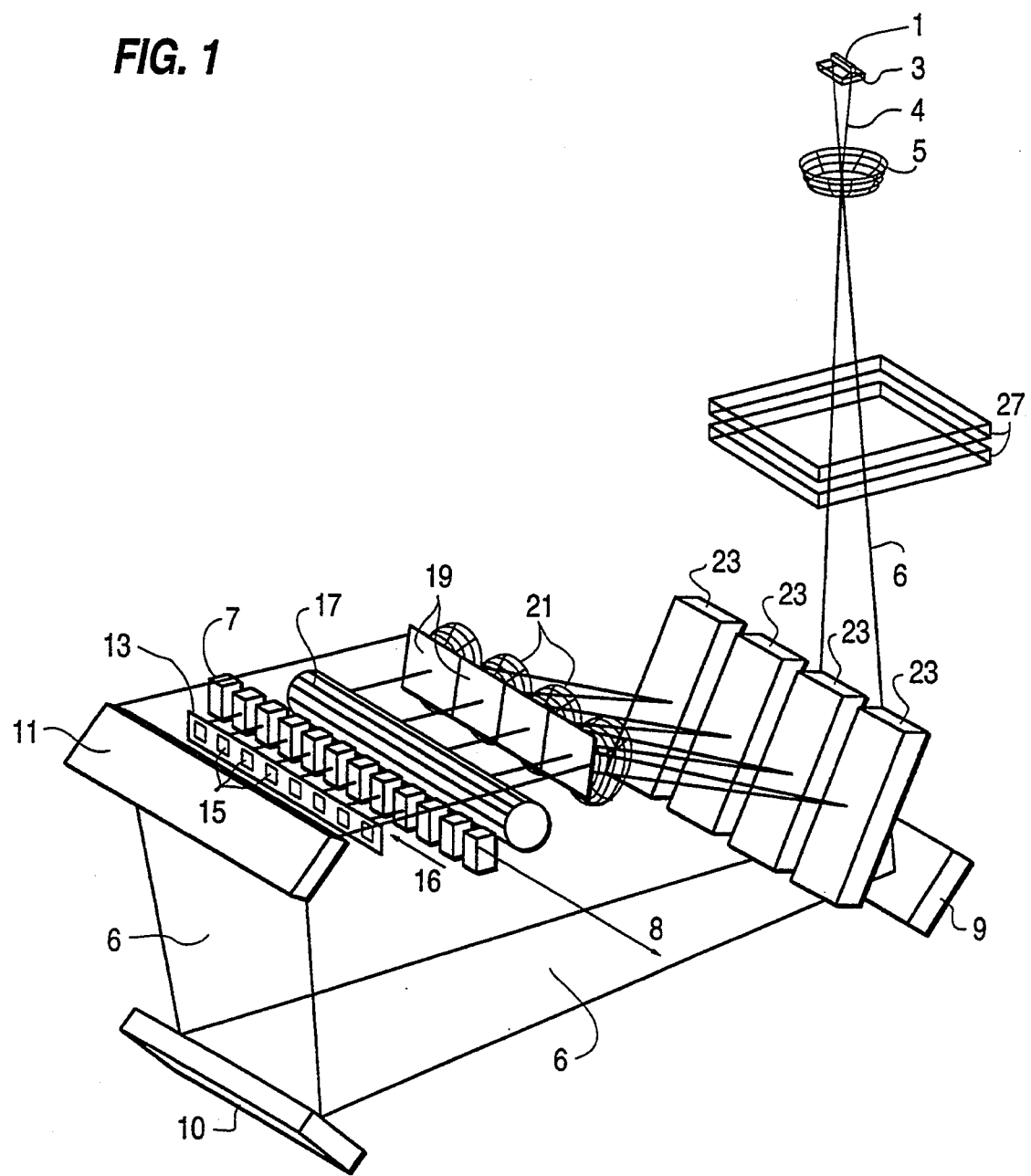
FIG. 1 is a schematic showing a known embodiment of an optical module.

FIG. 1 is a schematic of a multi-channel optical analyzer including the optical module. The multi-channel optical analyzer illustrated in FIG. 1 is described in greater detail in U.S. Pat. No. 5,002,392, which is incorporated herein by reference, and will only briefly be described herein to the extent necessary for understanding the present invention.

As shown in FIG. 1, a broadband spectral light source 1, such as a tungsten-halogen or a Xenon lamp, which may include a diffuser (not shown), projects light towards a slit forming device 3 which passes a beam 4 having the pattern of a slit. A short focal length collimator 5 follows the slit and is used to project the beam 4 in a pattern of a slit to infinity, thereby forming a slowly diverging beam 6. The slit length and collimator are chosen so that at a reasonable distance beam 6 has diverged to cover a plurality of reaction wells 7 containing the reaction volume (blood samples) to be optically monitored. Slit 3 may be formed, for example, of a stainless steel substrate 0.013 mm thick having an air slit width of 100 $\mu$m and length of 5.0 mm. Collimator 5 may be an Edmund Scientific Co. Achromat No. J32,319, which has a focal length of 35 mm, diameter of 25 mm, center thickness of 13.50 mm and which is anti-reflection coated with $\frac{1}{4}$ wavelength $M_gF_2$.

To make the optical system compact, beam 6 is folded a number of times by mirrors 9, 10 and 11 prior to being intercepted by a mask 13 having a plurality of openings 15 for dividing beam 6 into a plurality of individual beams 16 corresponding to the number of reaction wells 7 containing reaction volumes to be optically monitored. The divided beams are sized and spaced so that each beam passes through the desired portion of just one of the reaction wells 7. Reaction wells 7 are moved incrementally in the direction of arrow 8 from station to station, each station corresponding to the optical path of a respective one of the individual beams 16. The respective optical beams are also referred to herein as light channels. Although only 8 light channels are illustrated in FIG. 1, the number of light channels built into a machine is a design choice. For example in one implementation of the machine developed by the assignee of the present application, there were 15 light channels, meaning that there were 15 light beams formed by mask 13 and each reaction well of a cuvette was moved incrementally through each light channel, residing at each station or channel long enough for the reaction volume to be optically monitored to detect any change in the spectrum of the light beam transmitted therethrough.

After passing through reaction wells 7, beams 16 are intercepted by a rotating shutter 17 which sequentially passes the beams transmitted by the reaction volumes in reaction wells 7. The beams passing through shutter 17 are diffracted by transmitting diffraction gratings 19 in a known manner. FIG. 1 shows four diffraction gratings 19 followed by four corresponding focussing lenses 21 for focussing the diffracted beams onto four corresponding photodiode arrays 23. Again, the number of diffraction gratings, focussing lenses and photodiode arrays is a design choice depending on how the light channels are to be time shared. The diffraction gratings are preferably high dispersion, high efficiency transmission holographic diffraction gratings having a pitch of 0.8744 $\mu$m.

Photodiode arrays 23 are arranged so that the spectrum of each diffracted beam falls across the linearly arranged photodiode elements of a respective one of the arrays. The optics of the system are such that a central element of each array 23 is the optical conjugate of slit 3. Photodiode arrays 23 each develop electrical signals corresponding to the spectral distribution falling on the array. Photodetector arrays 23 are oriented so that the spectrum of the diffracted beams falls across the linearly arranged photodetector elements and the optics of the system are such that a central element of each array 23 is an optical conjugate of slit 3. Each photodetector array may include 35 identical photodiodes each covering a spectral range of 390 nm to 690 nm with a spectral resolution of 10 nm. Photodiode arrays of this type are available commercially from Hamamatsu Co. of Japan under part number S 2317-35Q. The light modifying wheel (LMW) 27 may be provided with an open position, a blocked (closed) position, a filter position in which the plurality of filters can be selectively inserted, and a position where a liquid crystal clot simulator (LCCS) is disposed in the light path. This liquid crystal clot simulator (LCCS) is described in U.S. Pat. No. 5,030,005, assigned to the assignee of the present application, hereby incorporated by reference.

Photodiode arrays 23 each develop electrical signals corresponding to the spectral distribution falling on the array. Arrays 23 are connected to scanning and recording electronics which sequentially scan the photodiodes for converting the electrical signals to digital signals and storing the digital signals in a computer memory, e.g., RAM or disk storage, for further processing and evaluation.

Figure 2A:
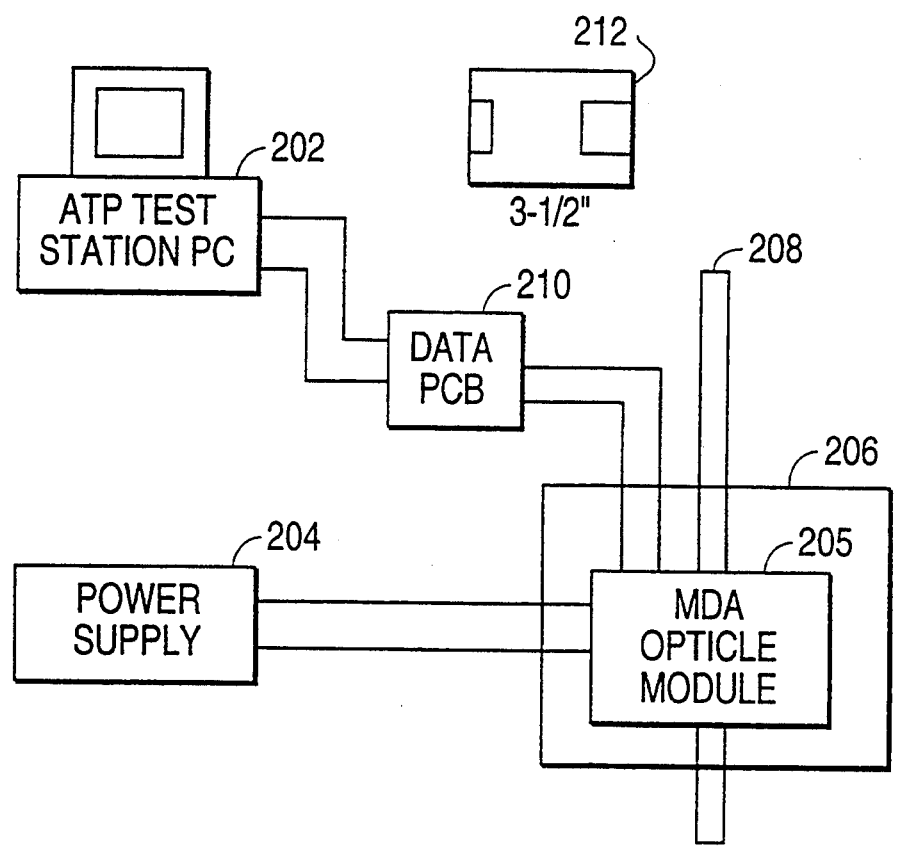
FIG. 2a is a block diagram of a test set-up for testing an optical module according to one embodiment of the invention.
Figure 2B:
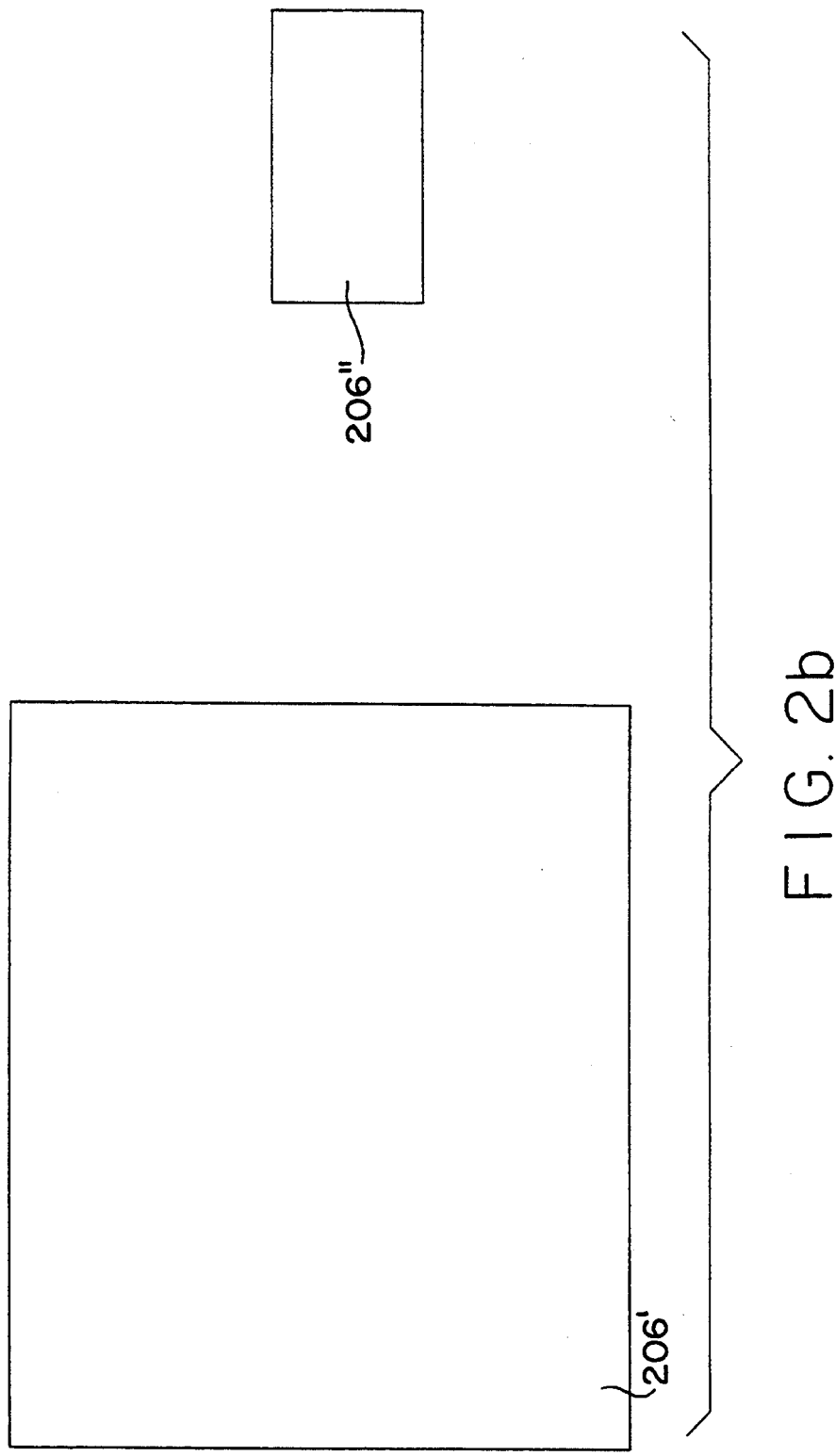
FIG. 2b shows the test covers with dimensions needed to perform the testing.

FIGS. 2a and 2b are a block diagram showing an arrangement for testing an MDA optical module. As shown, the materials needed to conduct the testing according to an embodiment of the invention are the automatic acceptance test procedure (ATP) test station personal computer (PC) 202, an MDA optics power supply with cable 204, an MDA optical module with lamp for testing 205, an optical covers 206, e.g., photographer's cloth, for the optical module 205 and track fixture 208, a printed circuit board (PCB) data acquisition interface board 210, a beam alignment fixture having 3 pieces and two screws (not shown), the automatic test procedure software on a 3½" floppy disk 212 (one per MDA optical module), and a set of 7 optical filters (not shown). Track fixture 208 simulates the track which carries the samples of material into the optical module of an MDA. Initially the track fixture 208, if it can be bolted to the optical module under test, verifies that the optical module will fit the MDA properly. The track fixture is also important in that it assures that the light beams are at the proper height where they will pass through the material to be analyzed, as described later with respect to the beam height test. In this way the fixture simulates actual operational mounting of the optical module on an MDA.

Setting up for the test procedure is as follows. With power off (and unplugged from power strip), install the lamp on the optical module, connect the lamp power supply to the lamp, connect the cable from the optical module external PCB (printed circuit board) to the light tower PCB (the optical module is shipped with these circuit boards disconnected), connect the power supply to the optical module via the two connectors, connect the ribbon cable from the ATP test station PC (including a data acquisition board) to the optical module, plug in the PC and the power supply to the power strip, plug in the power strip to a 120 vac wall outlet, turn the PC on and then turn the power strip on.

After the PC is turned on, the software will load and testing can proceed by following the instructions displayed on the PC. When all tests have been completed, shutting down proceeds as follows. Turn off the PC, turn off the power strip, disconnect the power supply and PC from optical module, if placing optical module back in packing carton then disconnect the connector from the external PCB to the tower PCB, remove the lamp and reinstall lamp hold down screws in optical module.

The test procedures will first be summarized and then explained in more detail. Alignment and diagnostic tests include the display of all photodiode array elements of any of 15 (for example) stations, the display of any photodiode array element for all stations, and wavelength registration testing. Qualification testing includes traceability through serial number.

Features of electrical systems tests include electrical dark current, electrical noise, digital to analog convertor (DAC) and analog to digital (AD) bit tests, precision shutter speed tests, and light modifying wheel (LMW) tests.

Features of optical dark testing include optical leakage and optical noise tests. Features of wavelength tests include range of wavelengths realized, wavelength resolution, and wavelength calibration tests. Features of optical signal testing include usable signal, illumination uniformity, optical stability, cross-talk, and beam height tests. Features of filter testing include Bg36 filter and LCCS (liquid crystal clot simulator) testing. Mechanical compatibility with a test fixture emulating the MDA mounting bracket is also confirmed. Appropriate test results and values may be recorded to disk for later use and analysis.

Acceptance test procedure (ATP) will now be described in more detail. The ATP is based on real time data acquisition by a PC 202 using a Burr-Brown Data Acquisition board. The software for performing the test procedures may be advantageously written in QuickBasic and may be run compiled or in the QuickBasic environment. The hardware requirements are as follows. A high speed PC, e.g., a 386 based PC operating at 40 MHz is needed to accept data as it is produced by the optical module. The PC should be equipped with at least a 40 megabyte hard disk, a 1.44 Meg 3½" disk drive, a VGA monitor and a Cyrix 387-40 coprocessor or equivalent. The PC should be configured (Config.sys file) to specify files=20 and buffers=20. A power supply system should provide +12 VDC @ 10 Amps, +28 VDC @ 4 Amps, and 110 VAC @ 0.5 Amps, and be equipped with appropriate connector cables (see FIG. 3).

Figure 3A:
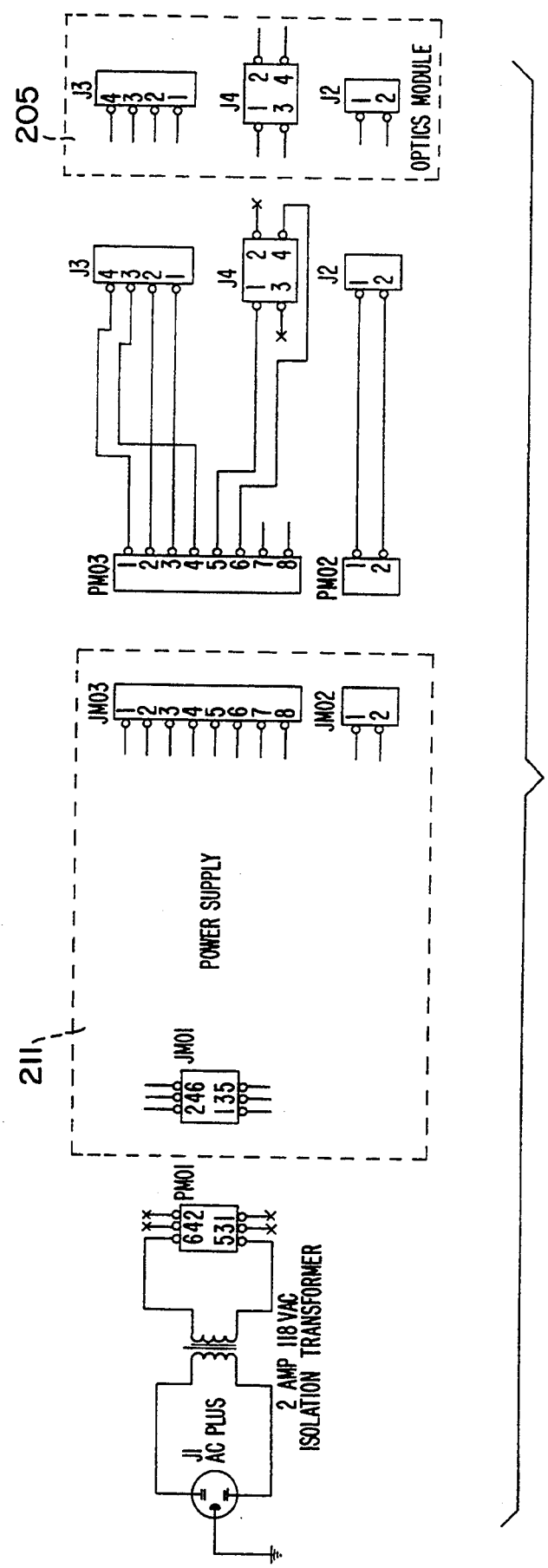
FIG. 3 shows the cables for use in the test set-up of FIG. 2.

The Burr-Brown Data Acquisition board is installed inside the PC and should be a PCI 20002C Carrier with digital input/output (I/O) with the following modifications: cut trace P1, pin 31; cut trace P1, pin 33; jump Fuse 2 to P1 pins 33 and 34, set address to D000: Switch Position 1 2 3 4 5 6 8 on (+), and 7 9 10 off (−); and install a 4.7K resistor from ground to each of P1 pins 19–29. The connector cable for the board (and the power supply) should be as shown in FIG. 3.

Software requirements are DOS 3.3 or higher (Required); QuickBasic Professional Ver 7.0 (used for development and changes only); and Masm, Microsoft Assembly Language Assembler Ver 5.0 or higher (used for development and changes only). The specification Appendix lists an embodiment of the testing software according to the invention.

A 3½" disk is shipped with each optical module. The disk must be formatted. It is advantageous to have only one disk for each MDA optical module, i.e., only data for one MDA optical module on each disk. The disk should accompany the MDA optical module for future consultation. It is recommended that at least one backup disk be maintained. The ATP test program will prompt the user for automatic back up to hard disk. If a serial number already exists on the floppy disk the user is so notified. If files exist under a sub-directory of the disk, the user has the option of recording over those files or replacing the disk.

Also required are other fixturing items: a photographer's cloth and track cover (FIG. 2b), track fixture, slider and gage, a set of spike (narrow bandpass) filters (Andover XXXFS10-25 or equivalent) of the following wavelengths: 405, 420, 450, 500, 546, 600, and 656 nm.

The procedure for implementing the features of the ATP includes Instrument (optical module) Traceability—the part number with revision letter and serial number of the optical module must be permanently marked on the back of each optical module.

Disk Files—at the end of an evaluation the floppy disk contains a serial number file, a log file, a criteria file and two files for each test run. Those files are automatically placed in the appropriate sub-directory listed above and are copied to the hard disk if desired under file directory C:\MDA\FILES\<Serial Number>.

A file "Serial.Num" is produced in the root directory to contain the serial number of the optical module under test. A log file under each location's subdirectory logs tests attempted and test results A file "Crit.prn", containing all the criteria from which tests are evaluated against, is copied from the hard disk to the tester's directory on the floppy disk. Two files, an Error file and a Results file, are produced for each of the following tests: Electrical Systems Check, Optical Dark Current, Optical Beam Alignment, Wavelength registration, Optical Profile, Bg36 Filter evaluation, and LCCS Evaluation. The Error file, one file for each test, includes a list of errors which caused a test to fail. The disk file combines the test name and an ".err" extension for the file name. The Result file, a second file for each test, includes test criteria and details of the performance for each photodiode of the array. The disk file combines the test name and a ".prn" extension. These ".prn" files are formatted to be imported into a spread sheet program, such as Lotus 123, as numbers.

Optical module testing proceeds as follows. Disk—The user is asked to insert a disk in drive "A:". The following subdirectories will be automatically added if they do not already exist: "KMC", "OKC", "DUR", and "TEST".

Code Name—The user is asked to enter a location code where applicable. The code for, for example, Kollsman is "KMC", Oklahoma is "OKC", Durham is "DUR", and Testing is "TEST". All files are placed in the appropriate subdirector, based on the location code.

Criteria—The criteria for each test, data file "C:\MDA\FILES\CRIT.XXX" (where XXX is a three character location code), are loaded at the beginning of the program. The entire file is copied to the user's sub-directory. Test specific criteria are recorded at the beginning of each test file.

Wavelength—If the disk has a reasonable wavelength registration file recorded then those parameters for determining wavelength are read.

Figure 4A:
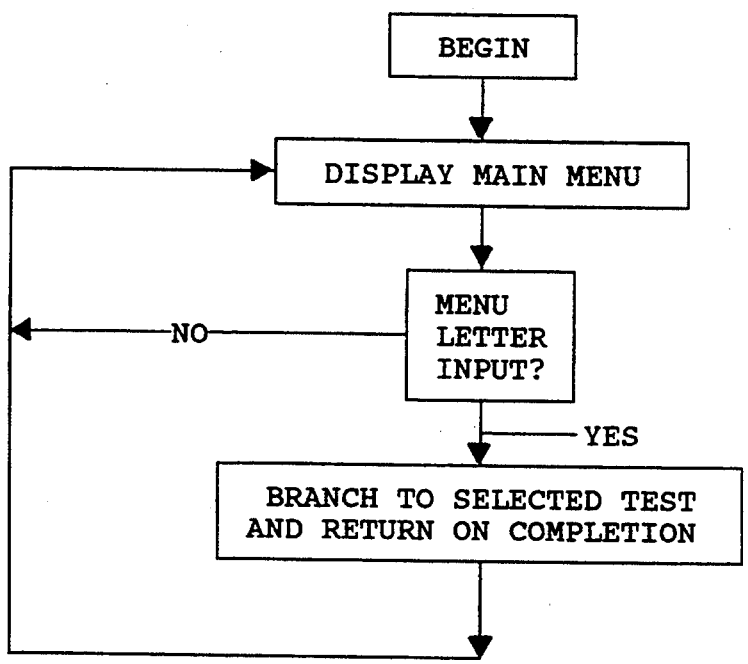
FIGS. 4a to 4o are flow charts for an embodiment of the menu driven test method according to an embodiment of the invention.
Figure 4B:
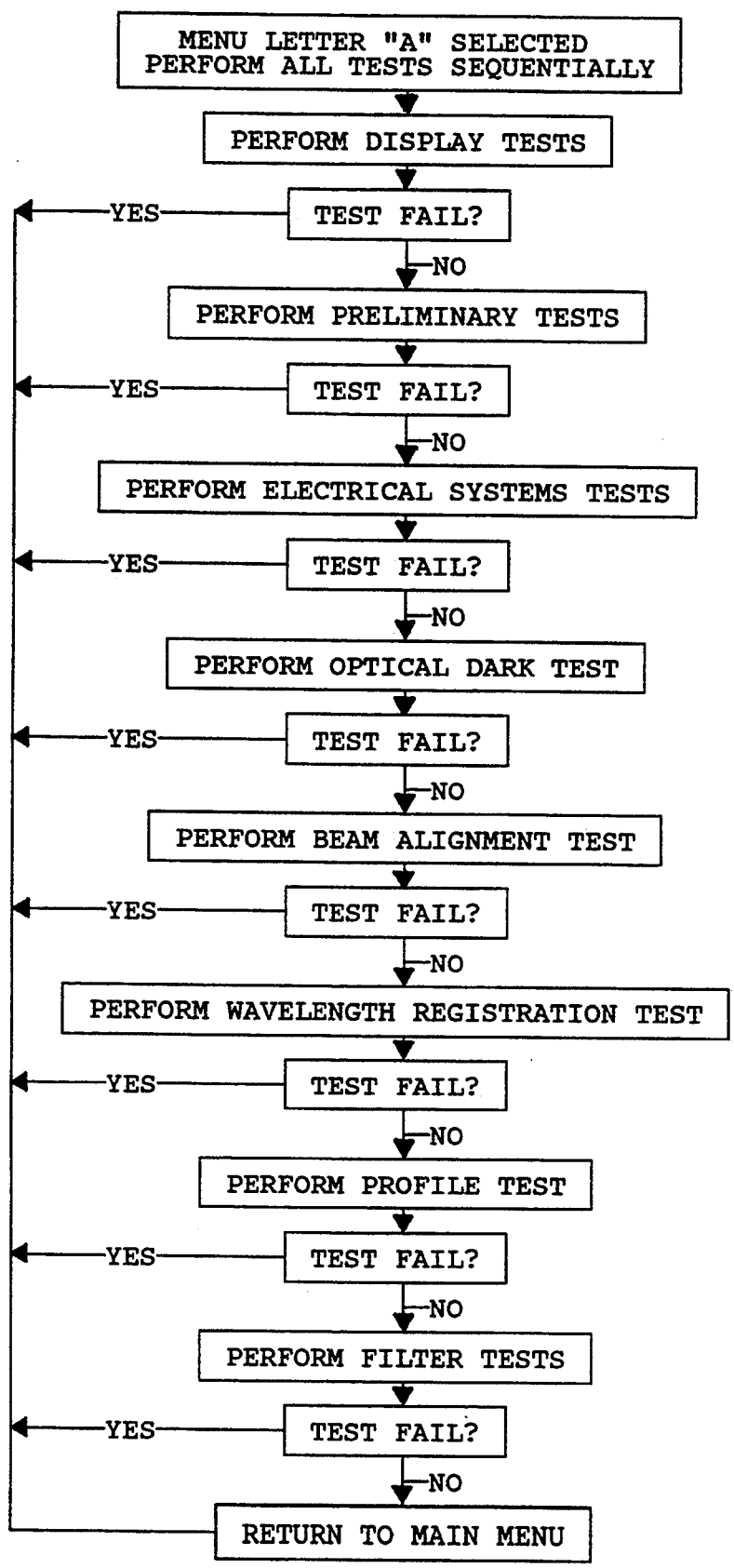

Menu—The user is presented with a menu from which to select tests (see FIG. 4a). The desired test is selected by pressing the corresponding letter. <Enter> need not be pressed after pressing the desired letter. The tests must be run contiguously in the order in which they appear in the menu. If the optical module fails a current test, the succeeding test will not run. If a test fails or if the program is interrupted, the user must begin testing at the beginning. Selecting "A" from the main menu will cause all tests to be run in order (see FIG. 4b).

Figure 4C:
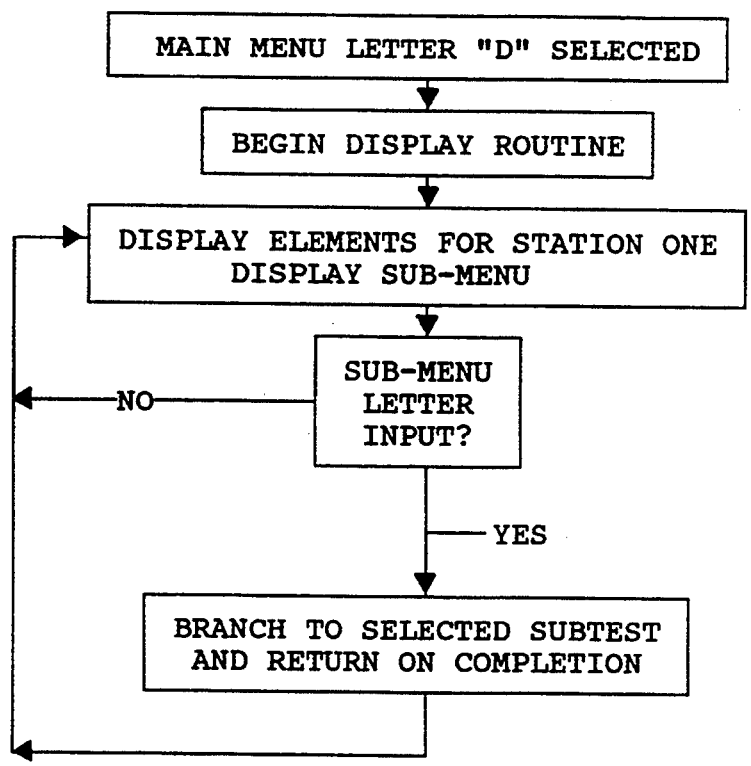

Specific tests will now be described in more detail. Display (FIG. 4c)—After selecting "D" from the main menu. a screen of 35 elements for position (station) one will be displayed (positional display). If wavelength has already been determined, each element will be displayed in the color of light on that element, otherwise all elements are displayed in white. The positional display visually indicates the output levels of the array elements, and may be take the form of color, intensity or height variations, for example, representing the different output levels. A user can thereby readily observe how an array and/or element is behaving.

A sub-menu is displayed on the right. Pressing sub-menu letter "E" (FIG. 4k) when the display is showing all elements of one station (position), changes the display from a positional display to a display of one element for all 15 positions (elemental display). Pressing "E" followed by a number and <enter> when the display is already in the elemental mode allows the user to jump to any corresponding element number. Pressing the <right arrow> key in the elemental mode increments the element number being displayed by 1. Pressing the <left arrow> key in the elemental mode decrements the element number being displayed by one.

Pressing "P" when the display is showing one element for all positions, changes the display from a elemental display back to a display of all elements for one position. Pressing "P" followed by a number and <enter> when the display is in the positional mode allows the user to jump to any position number. Pressing the <right arrow> key in the positional mode increments the position number being displayed by 1. Pressing the <left arrow> key in the positional mode decrements the position number being displayed by one.

Pressing "E" followed by a number and <enter> when the display is in the positional mode allows the user to select any corresponding element number. Subsequently pressing the <right arrow> key in this mode increments the element number selected by 1, and pressing the <left arrow> key decrements the element number selected by one.

The gain of an element signal amplifier is typically preset to 170/4095, however any gain may be selected as desired. A gain of 170/4095 is selected to provide an adequate dynamic range, so that at maximum element output signal levels, the element signal amplifiers remain unsaturated. Pressing sub-menu letter "G" (see FIG. 4l) followed by a number and <enter> changes the gain to the number entered divided by 4095. Pressing the <up arrow> key increments the gain by 10. Pressing the <down arrow> key decrements the gain by 10.

Pressing sub-menu letter "N" (FIG. 4l) normalizes the array signal to a preprogrammed (not user selectable) value by mathematical selection of individual elemental gain values. Pressing "G" followed by a number, <up arrow>, or <down arrow>, restores the gain to a constant value.

Pressing sub-menu letter "S" (FIG. 4m) changes the y axis scale to display from 0 to 270 only. This is used to evaluate dark and very low light levels. Pressing sub-menu letter "S" a second time returns the scale to normal (0 to 4000). Pressing sub-menu letter "W" (FIG. 4n) causes the light modifying wheel to increment position by one. Pressing sub-menu letter "Q" (FIG. 4o) or any other undefined key returns the user to the main menu.

Figure 4D:
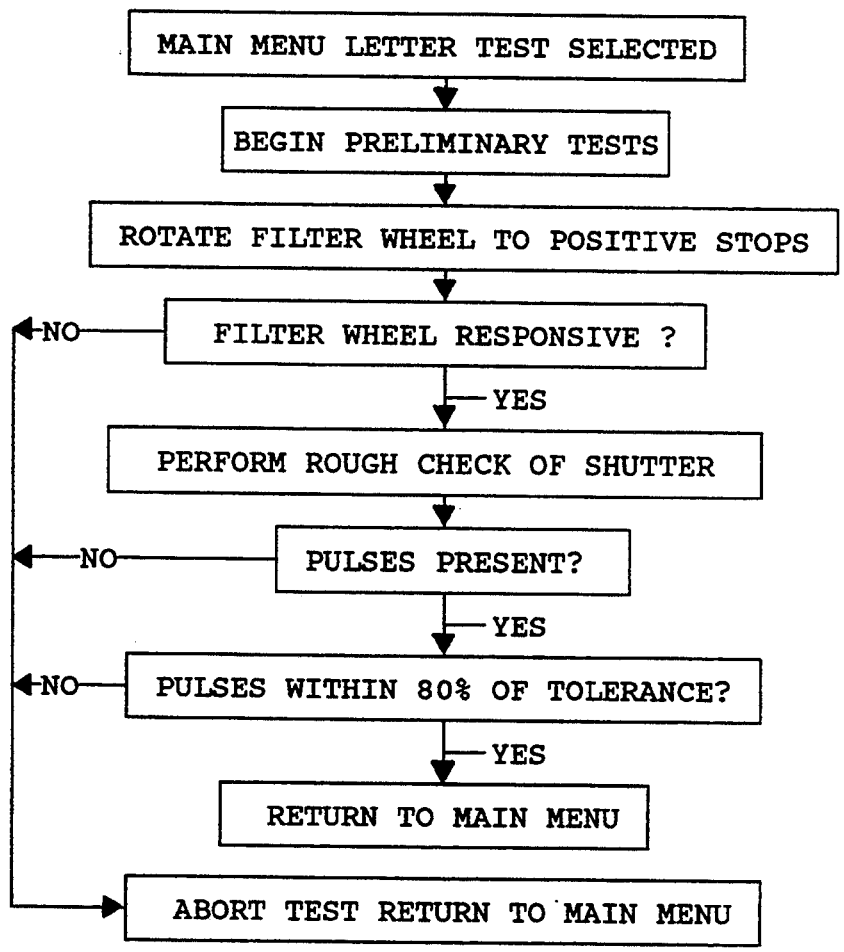

Preliminary testing will now be described (see FIG. 4d). These tests are done automatically to ensure that the other tests described below are capable of running, that is, that the shutter is running and the LMF is operating. First, the light modifying wheel is rotated in turn to both positive stops which ensures that the light modifying wheel is responsive, and then a rough check of the shutter is performed to see if pulses are present and within 80% of tolerance.

Figure 4E:
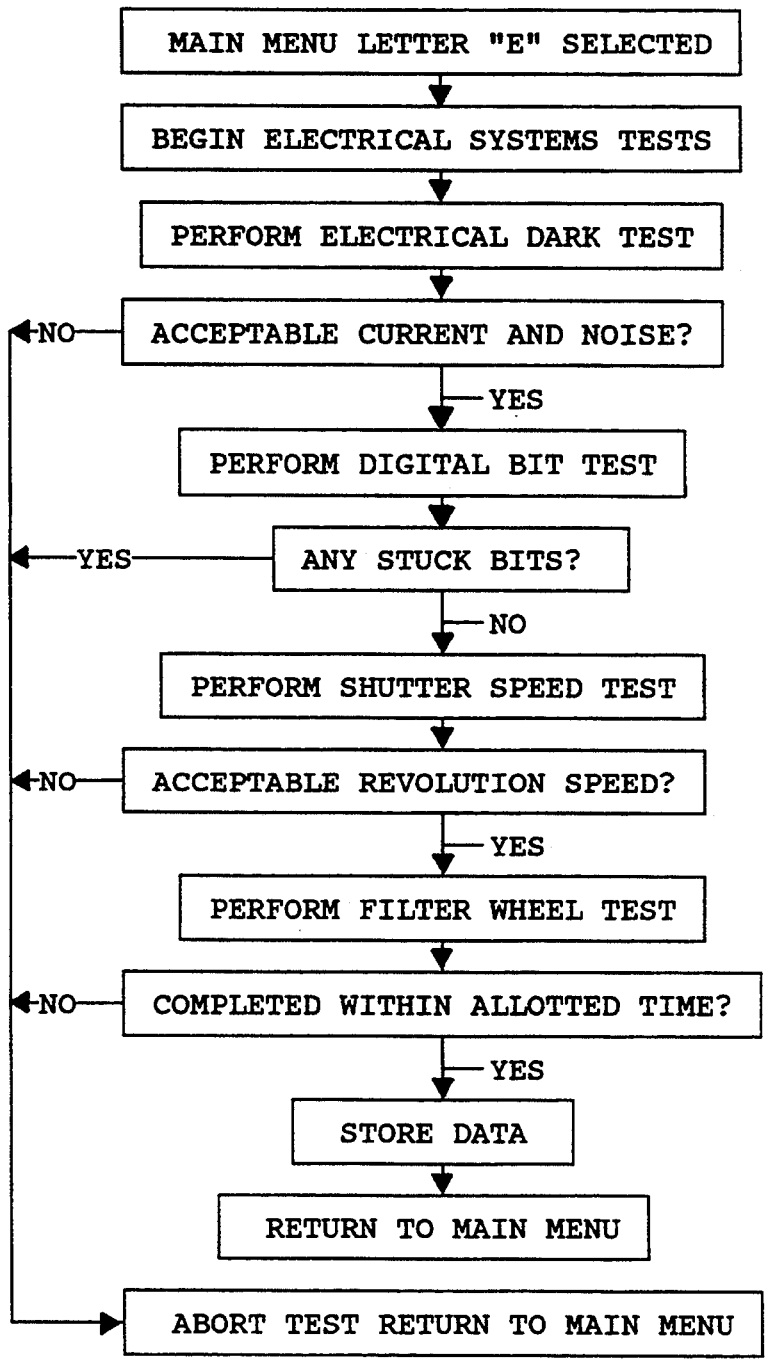

Electrical systems tests will now be described (see FIG. 4e). These tests are to determine basic electronics operations. Electrical Dark Test—This test checks the performance of the electronics used in the detection of optical signal. Dark current levels and electronic noise are measured. The user is instructed to disconnect the lamp (or turn off the lamp supply) and cover the optical module so as to eliminate any ambient light. The ATP scans the photodiode array 100 times. After each scan, a rolling sum and rolling standard deviation is calculated. At the end of 100 scans, the average for each photodiode element is compared to a minimum and a maximum signal level and the standard deviation is compared to a maximum RMS noise level.

The variables LOWEDK and MAXEDK define the lower and upper limits of acceptable dark current in the program criteria. NOISYEDK defines the maximum RMS noise acceptable. A minimum signal of 0 counts, a maximum signal of 100 counts and a maximum RMS noise of 2.5 counts is acceptable.

Digital bit testing, an electrical systems test, will now be described. The gain DAC, A to D converter, and interface are checked for "stuck" bits, i.e., bits that will not change, "toggle," from logical "1" to "0" or vice versa. The DAC is checked by first normalizing the signal. Then the DAC values are checked to ensure that each bit toggled at least once. Next the A to D converter is checked. After setting a constant gain, the detectors are scanned and the values are checked to ensure that each bit toggled at least once.

The shutter speed test, an electrical systems test, is now described. The ATP counts interrupts by polling the interrupt signal as a digital I/O TTL signal. In order to test for required accuracy with the current digital resolution, this test runs silently for 5 minutes. After 5 minutes, the number of interrupts counted is divided by the PC clock timer. The program variable RPSTIME is defined as the criteria for the length of time the test must run in order to achieve the desired resolution. The variables HIGHRPS and LOWRPS define the upper and lower acceptable limits. A calculated speed of 5.00 RPS ($\pm 0.1$ RPS) is acceptable.

Light modifying wheel testing, an electrical systems test, is now described. A complete test is performed by commanding the wheel to move clockwise to each of the next 3 positions and then back counterclockwise to each of 3 positions. Any move must be completed within a prescribed time period, e.g., 5 seconds. Any failure causes the test to halt.

After the electrical systems tests are completed successfully, data associated therewith is stored. Otherwise, flow returns to the main menu display.

Figure 4F:
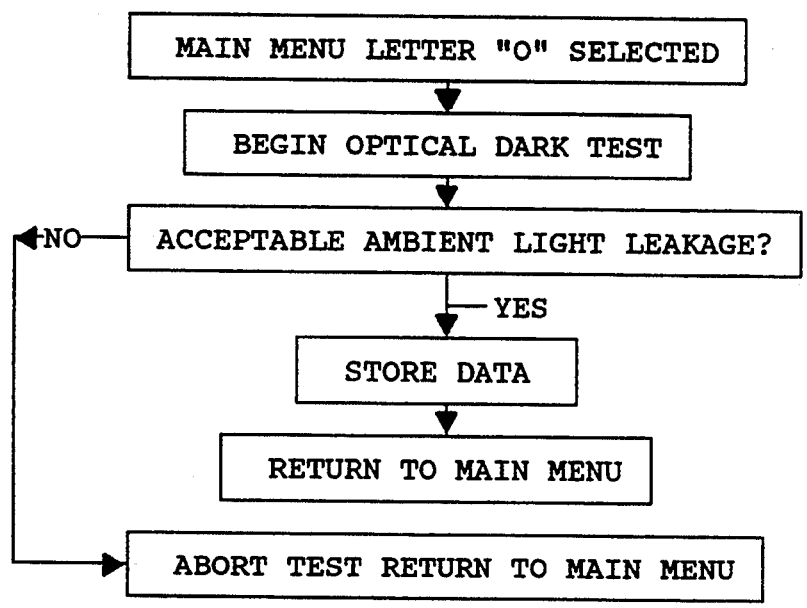

The optical dark test (see FIG. 4f) is used to determine the amount of ambient light leaking though the box, i.e., the optical module cabinet. The user is instructed to reconnect the lamp (or turn on the lamp supply) and cover only the optical module track area. This test should be performed in a normally lit room so as to measure the effect of ambient light from all sources. The ATP scans the photodiode array 100 times. After each scan a rolling sum, and rolling standard deviation for each photodiode element is calculated. At the end of 100 scans, the average for each photodiode element is compared to a minimum and a maximum signal level and the standard deviations are compared to a maximum RMS noise level. The variables LOWODK AND HIGHODK define the lower and upper levels of acceptable ambient light in the program criteria. NOISYODK defines the maximum RMS noise acceptable. A minimum signal of 0 counts, a maximum signal of 100 counts and a maximum RMS noise of 2.5 counts is acceptable.

Figure 4G:
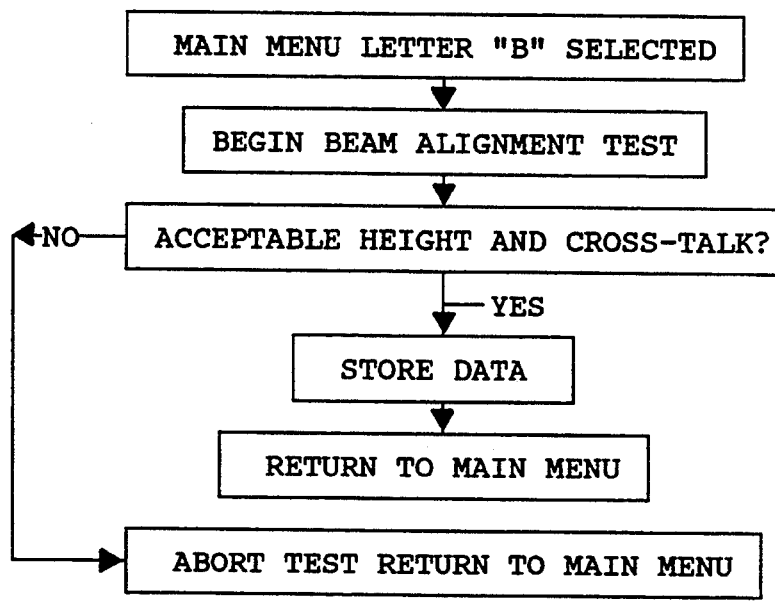

The beam alignment test (see FIG. 4g) determines how much light for one optical channel is bleeding onto another optical channel's detector (cross talk) and whether the height of the beam is within tolerance (beam height). The track fixture is important in determining the proper beam height, as mentioned above. The user is instructed to be sure the lamp is on and that the track is reasonably covered. The ATP then measures dark current for 10 scans with the light modifying wheel in the blocked position. The average of the 10 scans is ZDARK, for each element. The user is now instructed to place a blocking device known as a slider, for blocking one or more optical channels with both adjacent channels unobstructed, in the track with the slider placed in the track fixture as far left (away from the shutter motor) as possible. Signal gain for each element is at maximum (4095/4095). The average of the raw signal (RAW) from 10 scans minus ZDARK becomes ZCROSS (cross-talk) for each blocked element:

$$ZCROSS = RAW - ZDARK$$

The user is instructed to place the slider in the middle position and finally in the full right position. Similarly, the average of the signal from 10 scans minus the dark current becomes ZCROSS for each of the new sets of blocked elements. The ATP compares the normal signal ZNORM to ZCROSS with the predefined maximum crosstalk, defined in the program criteria as MAXCROSS. The maximum crosstalk to signal acceptable is 0.1%. The user is now instructed to place the beam height gage in the center position. The signal without the gage is compared to the signal with the gage. No more than 99% difference in signal intensity is acceptable.

Figure 4H:
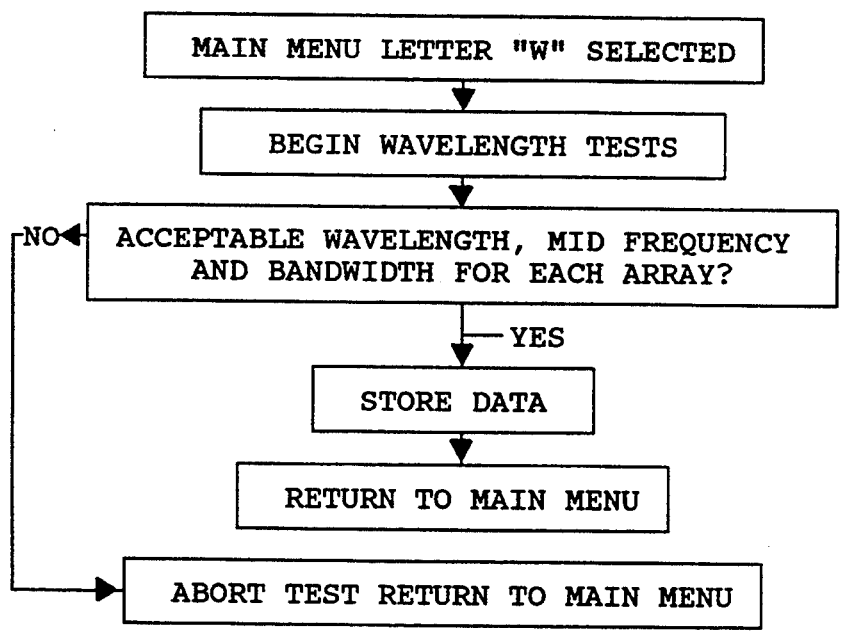

The wavelength registration test (see FIG. 4h) determines the wavelength mid-frequency and bandwidth for each detector of an array. The user is instructed to be sure the lamp is on and that the track is reasonably covered. The ATP then measures dark current for 10 scans with the light modifying wheel in the blocked position. The average of the 10 scans is ZDARK for each element. A preliminary profile test is performed to ensure that a reasonable amount of light can be sensed by each detector. The profile minimum is about ½ of the final required value as defined in the program as MINPRO where MINPRO = ½(ZPR00 + ZPR01*X + ZPR02*X^2 + ZPR03*X^3 + ZPR04*X^4 + ZPR05*X^5 + ZPR06*X^6 + ZPR07*X^7 + ZPR08*X^8), and where:

| | |
|---|---|
| ZPRO0 = −139.78, | ZPRO1 = 148.51, |
| ZPRO2 = −55.276, | ZPRO3 = 10.446, |
| ZPRO4 = −0.99866, | ZPRO5 = 0.055139, |
| ZPRO6 = −0.0017867, | ZPRO7 = 3.1212E-5, |
| ZPRO8 = −2.2519E-7 | | and X is the index into the detector array for elements 1 through 35.

The signal is then normalized by the ATP by selecting individual gain values for each element so as to balance the signal at a preprogrammed (not user selectable) level. For each of seven filters, the peak is found by fitting a Gaussian curve to the signal detected with a filter in place. The user is asked to confirm that the peak for each position is reasonable. The user then has the option to reposition the filter and try again (by pressing "R") abort the wavelength determination, (by pressing "A"), or continuing (by pressing "Y"). After all filters have been evaluated a linear regression is determined by a least squares fit.

The test passes if the calculated smallest wavelength (element 1) is less than or equal to the specified low wavelength, the calculated largest wavelength (element 35) is greater than or equal to the specified high wavelength, and the residual of each regression is greater than the criteria minimum. The maximum acceptable low wavelength is defined in the program as LOWWVLNTH. The minimum high wavelength is HIGHWVLNTH, and the correlation coefficient is defined as ZRESIDUAL. For example, the maximum acceptable low wavelength may be 395 nM, the minimum acceptable high wavelength 710 nM, and the correlation coefficient (R-2) greater than 0.9992.

Figure 4I:
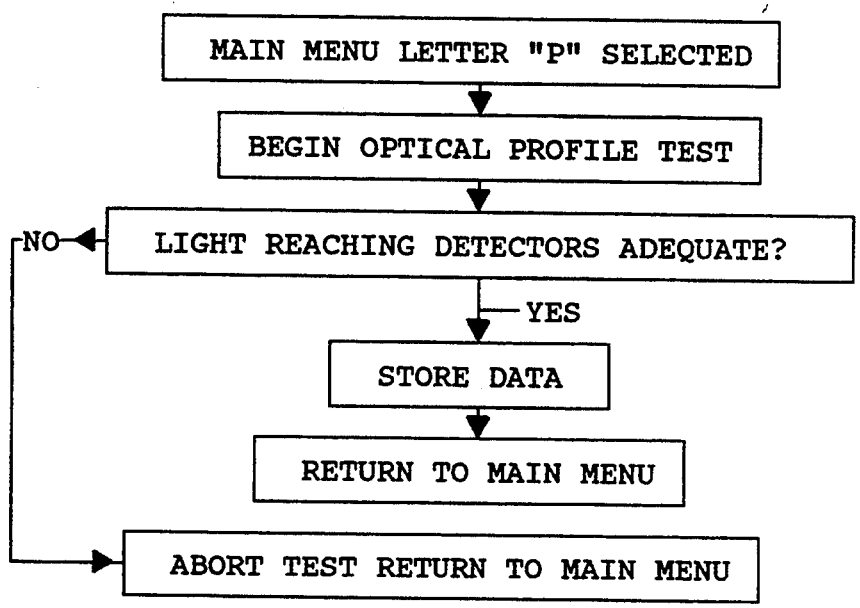

The optical profile test (see FIG. 4i) measures the amount of light reaching the detectors and the signal to noise ratio for each of 15 optical channels under normal operating conditions. The user is instructed to be sure the lamp is on and that the track is reasonably covered. The ATP then measures dark current for 10 scans with the light modifying wheel in the blocked position. The average of the 10 scans divided by its gain value (4095) becomes ZDARK for each element. The gain is then set to 170/4095 for all optical channels. The ATP calculates an element number based on each of 32 wavelengths to test. The signal value for each wavelength is interpolated from the closest discrete elements corresponding to the desired wavelength.

The average of the 10 scans is compared with a maximum value (not saturated) and with a minimum value calculated using a polynomial based on a typical signal defined at the beginning of the program. The signal divided by the standard deviation of each element:

ZAVG/ZRMS is likewise compared to a maximum optical RMS noise value. This comparison ensures that the combination of noise sources (electrical noise, optical noise, and shutter motor instability) will not significantly distort the usable signal. The minimum signal is calculated in the program as MINPRO where MINPRO=ZPR00+ZPR01*X+ZPR02*X ^ 2+ZPR03*-X ^ 3+ZPR04*−X ^ 4+ZPR05*X ^ 5+ZPR06*X-^ 6+ZPR07*X ^ 7+ZPR08*X ^ 8, and where

| | |
|---|---|
| ZPR0O = −139.78, | ZPRO1 = 148.51, |
| ZPRO2 = −55.276, | ZPRO3 = 10.446, |
| ZPRO4 = −0.99866, | ZPRO5 = 0.055139, |
| ZPRO6 = −0.0017867, | ZPRO7 = 3.1212E-5, |
| ZPRO8 = −2.2519E-7 | | and X is the element index into the detector array for wavelengths every 10 nm from 400 nm to 710 nm.

The maximum is defined in the program criteria as MAXPRO where MAXPRO=4000 counts. The minimum signal to noise ratio is defined as MINS2N such that
MINS2N=ZS2N0+ZS2N1−*X+ZS2N2*X ^ 2+Z-S2N3*X ^ 3+ZS2N4*X ^ 4+ZS2N5*X ^ 5+ZS2N6*-X ^ 6+ZS2N7*X ^ 7+ZS2N8*X ^ 8, and where:

| | |
|---|---|
| ZS2N0 = −221, | ZS2N1 = 296.43, |
| ZS2N2 = −126.41, | ZS2N3 = 28.16, |
| ZS2N4 = −3.0109, | ZS2N5 = 0.17263, |
| ZS2N6 = −0.0054823, | ZS2N7 = 9.104E-5, |
| ZS2N8 = −6.1752E-7 | | and X is the element index into the detector array for wavelengths every 10 nm from 400 nm to 710 nm.

Figure 4J:
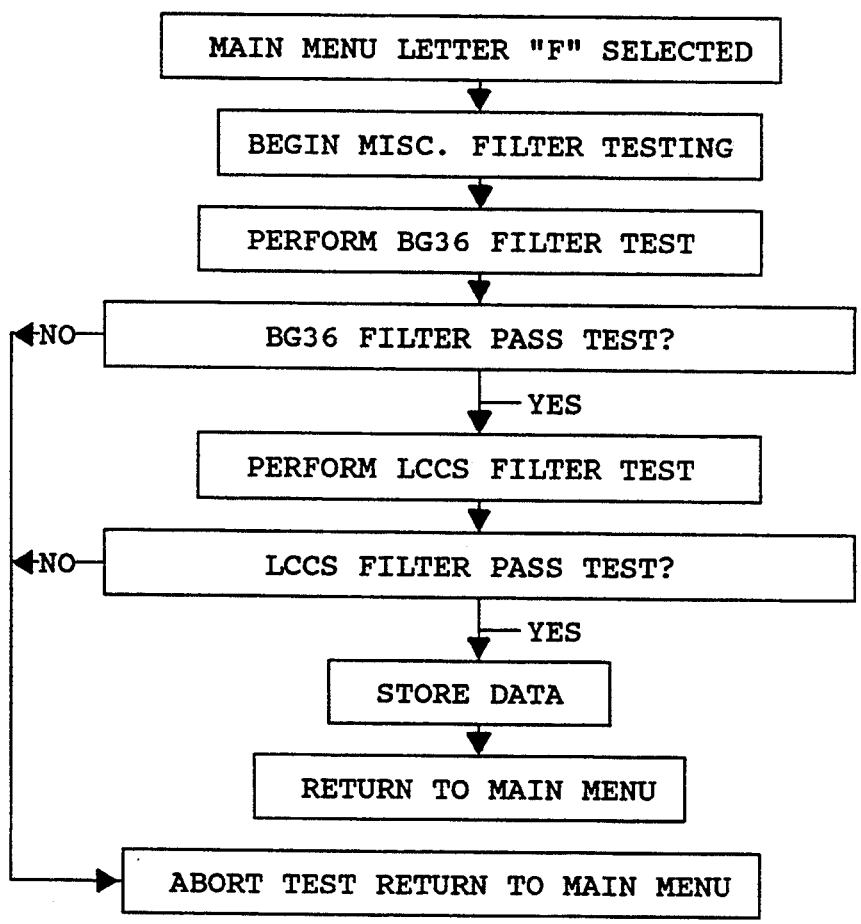
Figure 4K:
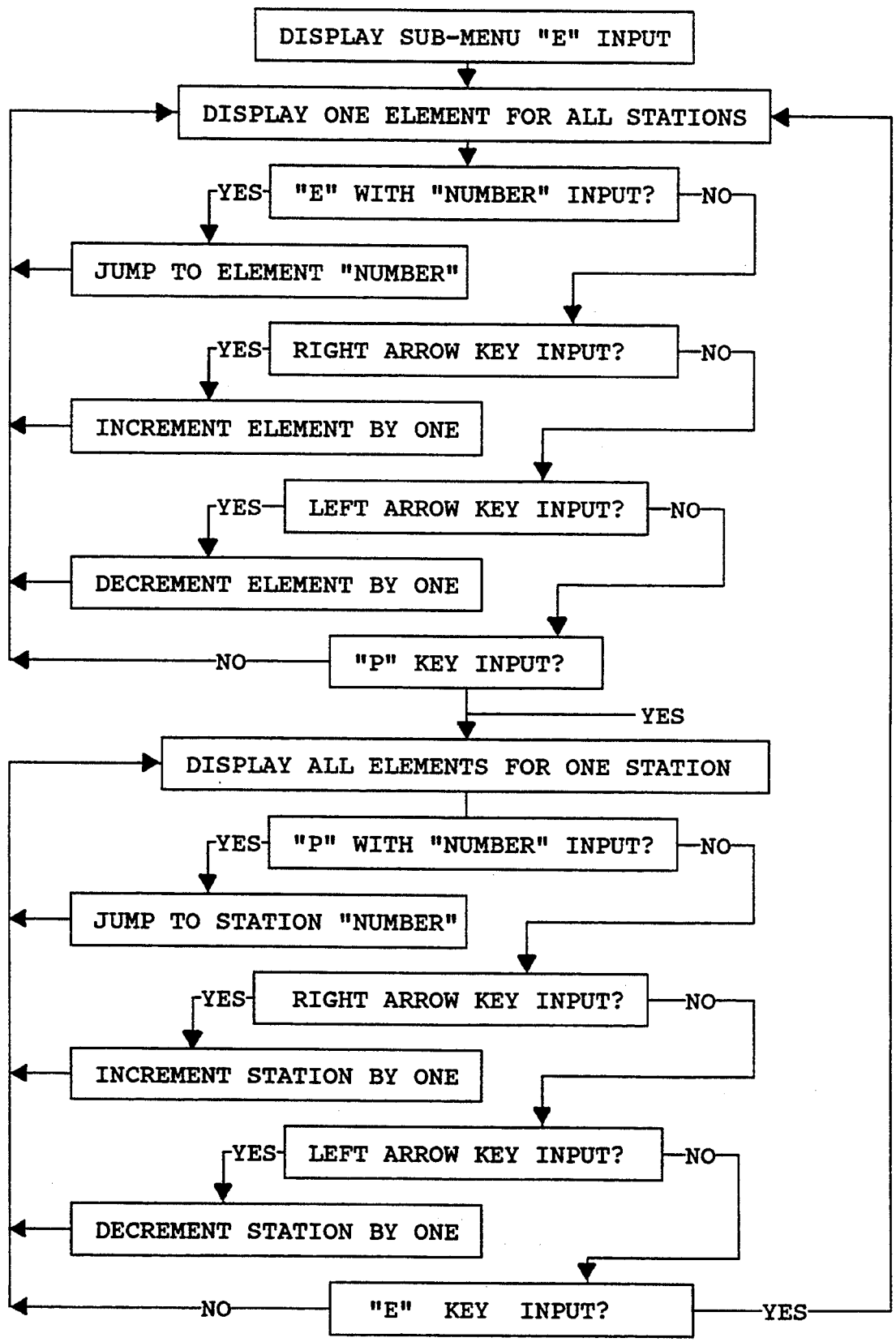
Figure 41:
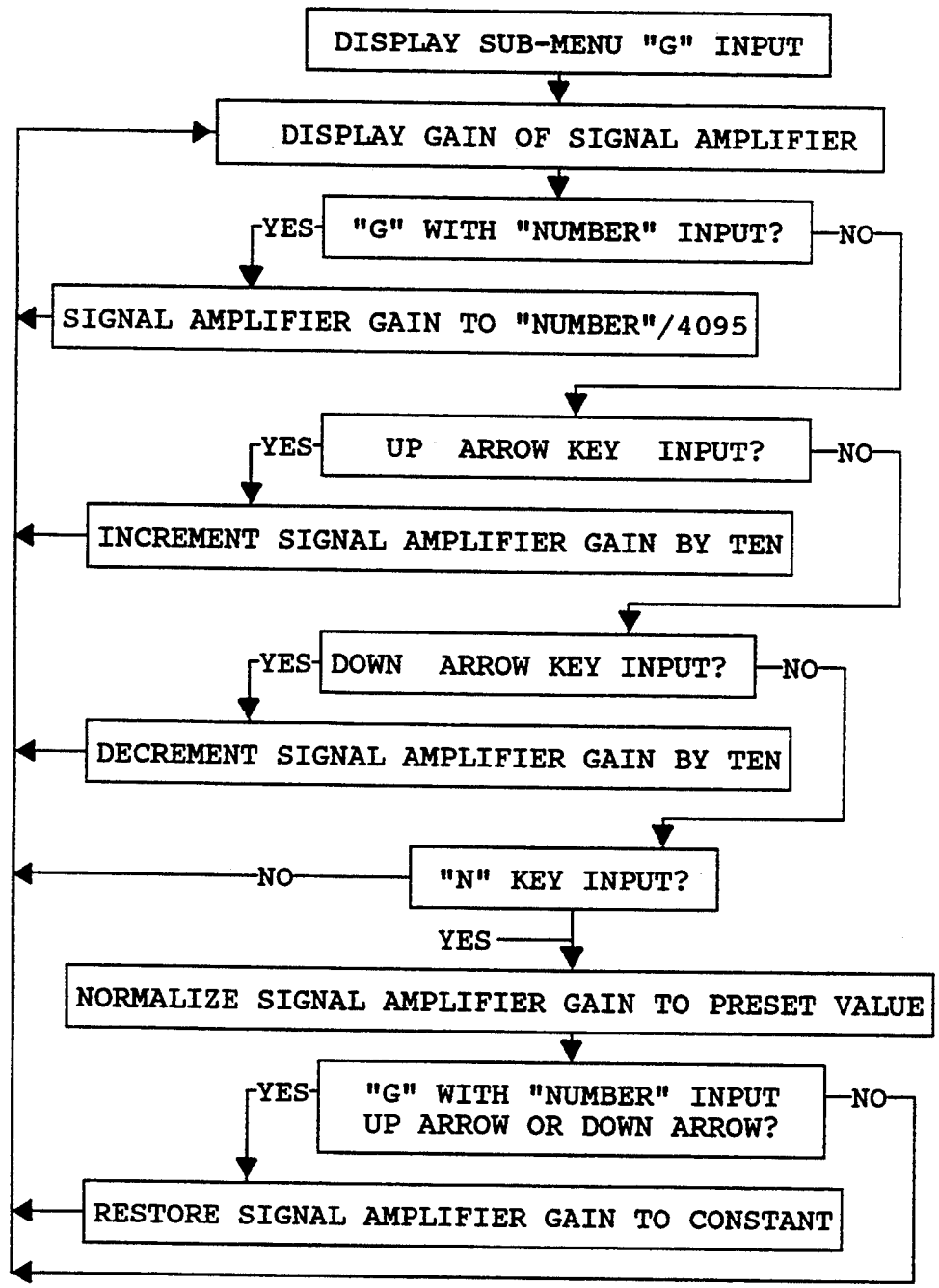
Figure 4M:
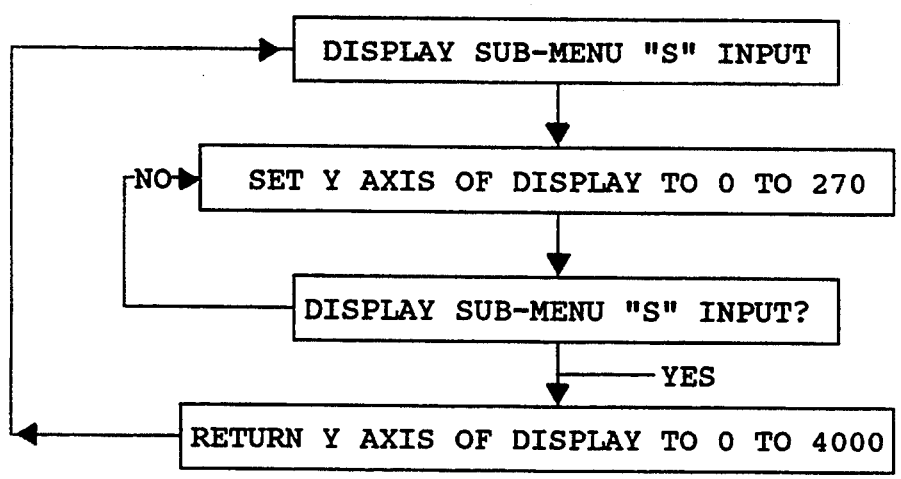
Figure 4N:
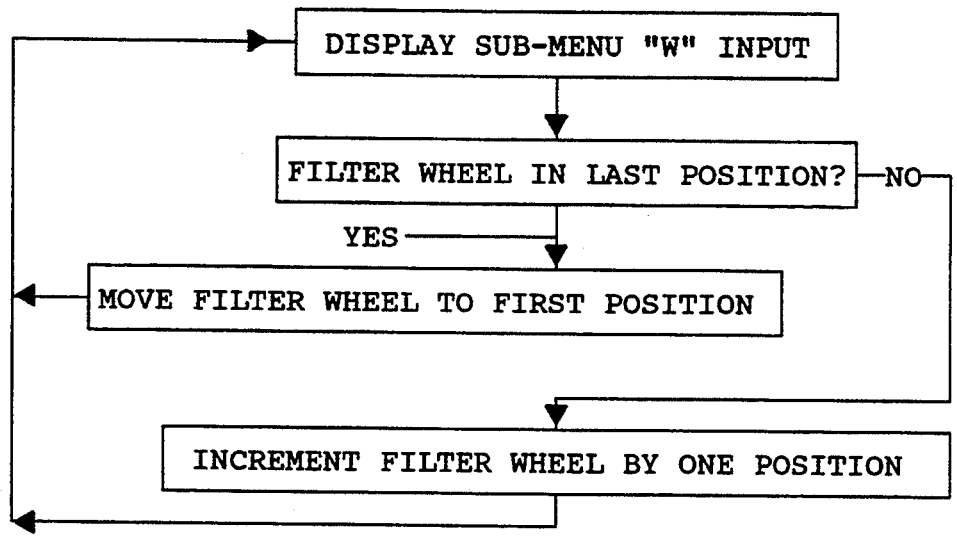
Figure 4O:
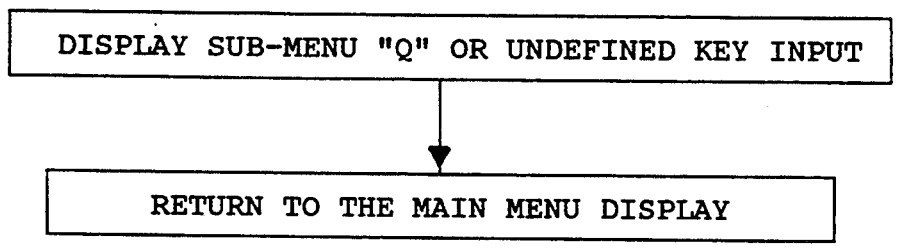
Figure 5A:
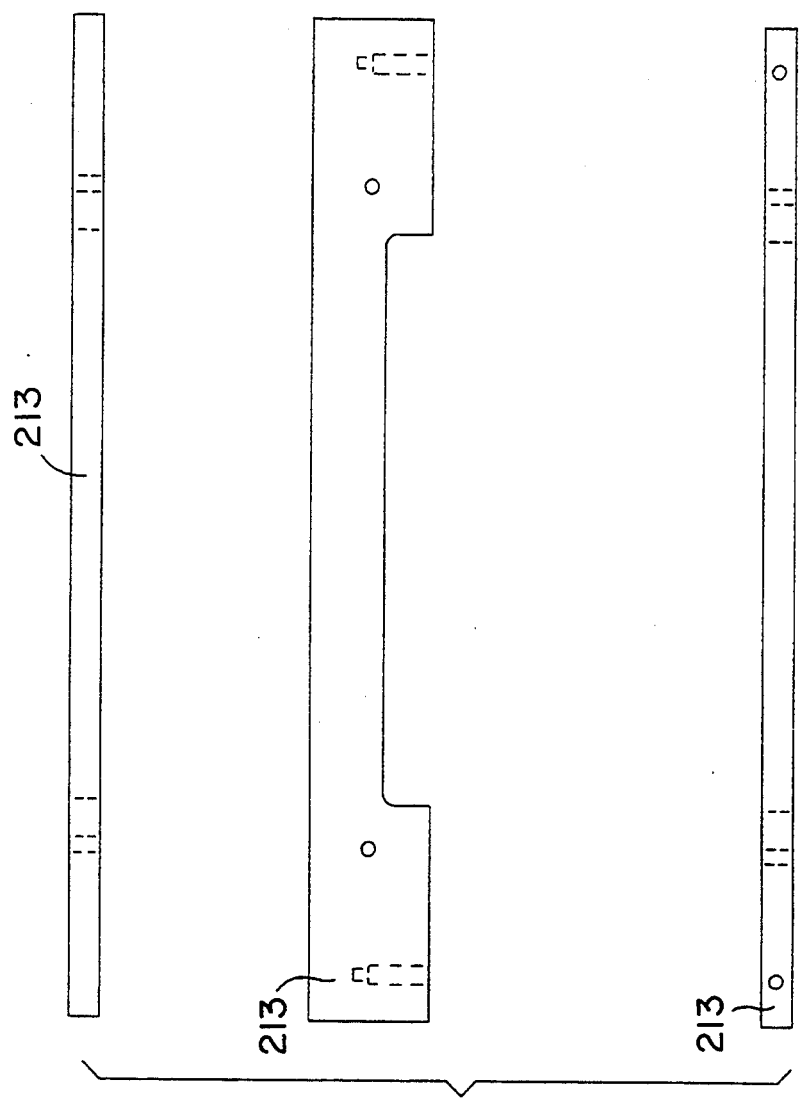
FIGS. 5a to 5h illustrate the component parts of a mounting fixture for mounting the optical module during testing.
Figure 5B:
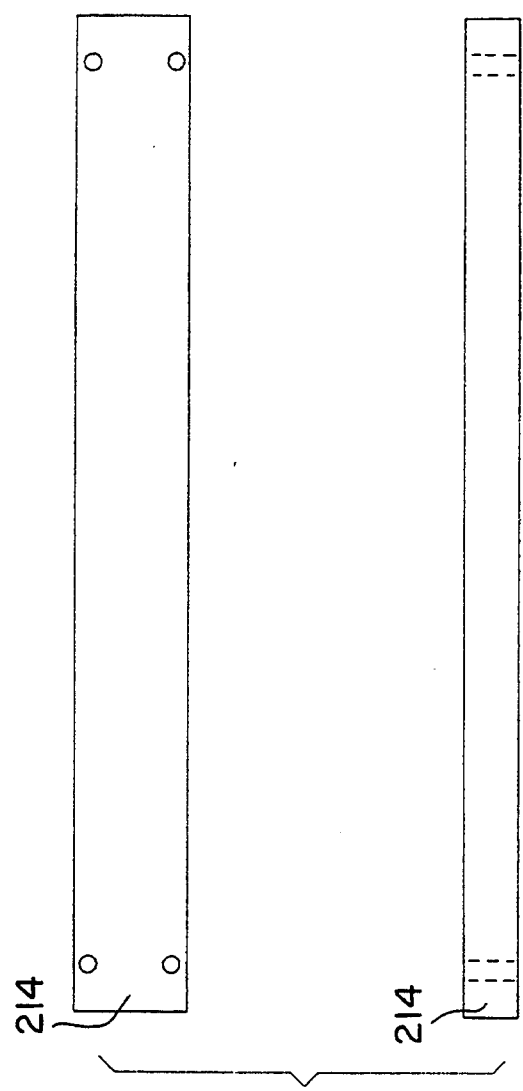
Figure 5C:
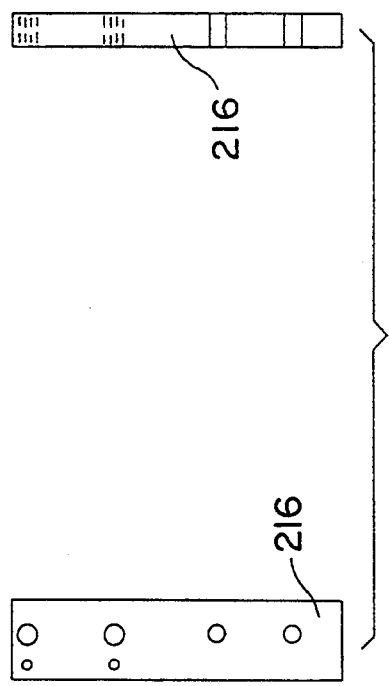
Figure 5E:
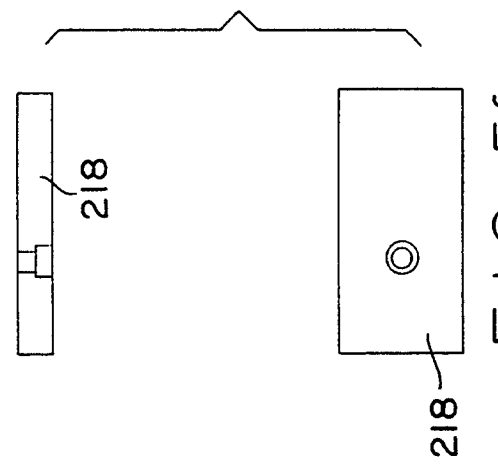
Figure 5D:
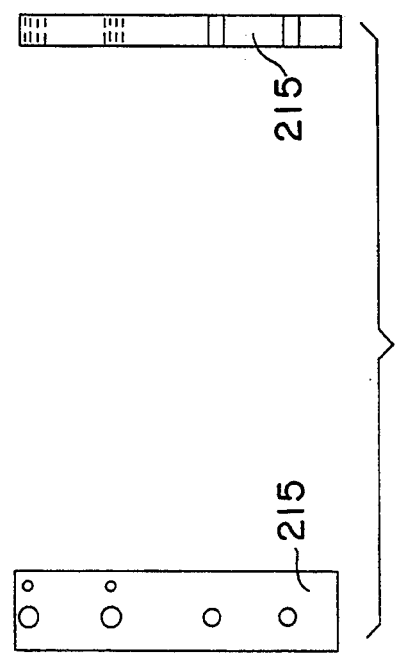
Figure 5F:
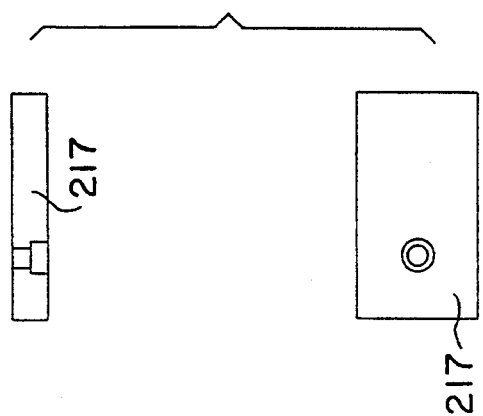
Figure 5G:
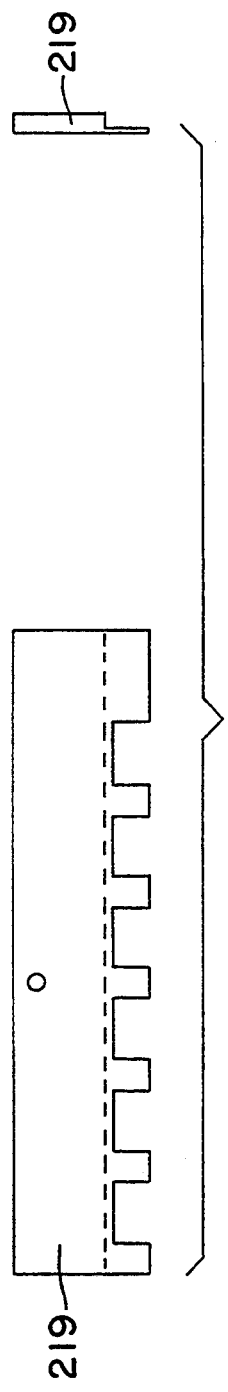
Figure 5H:
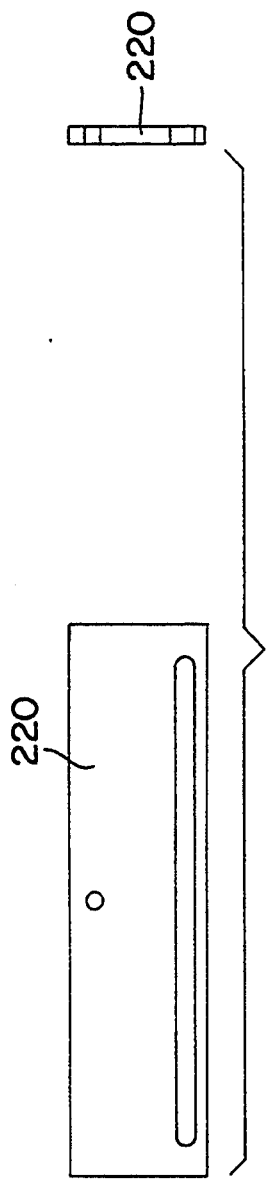

The filter testing (FIG. 4j) covers the two miscellaneous filters in the MDA optical module the BG36, filter and the LCCS filter. For both tests the user is instructed to be sure the lamp is on and that the track is reasonably covered. The ATP then measures dark current for 10 scans with the light modifying wheel in the blocked position. The average of the 10 scans is ZDARK for each element.

The signal is then normalized by the ATP by selecting individual gain values for each element so as to balance the signal at a preprogrammed (not user selectable) level.

BG36 Filter—The light modifying wheel is set in the BG36 filter position. At each of three wavelengths (493 nM, 548 nM, and 653 nM), the peak is found by fitting a Gaussian curve to the signal detected around the element expected to show a peak for that wavelength. The test passes if the calculated element for each wavelength corresponds to the calculated element determined by the wavelength determination found in the wavelength registration test. This variation in the realized element and the calculated element is defined in the program criteria as MINBG36 and MAXBG36. The maximum variation from the calculated element to the realized element is 0.25 elements.

LCCS Filter—The light modifying wheel is set in the LCCS position. At each of three commanded LCCS levels (low, mid, and high), the average signal of 10 scans is compared to an expected value at element number 21. The error between the expected signal level (LCCS$(LEVEL,EXPECT)) and the measured signal level is calculated in the program and compared with the criteria, LCCS$(LEVEL,TOLERANCE) for each of three levels.

The component parts and the assembly of a mounting fixture used during testing the optical module are shown in FIGS. 5 and 6. All of the parts are made of stainless steel. FIG. 5a shows the dimensions of part 1, of which two are required. FIG. 5b shows the dimensions of part 2, of which one is required. FIG. 5c shows the dimensions of part 3, of which one is required. FIG. 5d shows the dimensions of part 4, of which one is required. FIGS. 5e and 5f show parts 5 and 6 respectively, of which one each is required. FIG. 5g shows the dimensions of part 7, of which one is required. FIG. 5h shows the dimensions of part 8, of which one is required.

FIG. 6a shows a first portion of the assembly of the component parts of FIGS. 5, FIG. 6b showing a detail of FIG. 6a. FIGS. 6c, 6d, 6e and 6f show other portions of the assembly of the parts of FIGS. 5.

The apparatus and method for testing the optical module of an MDA device, in particular, for performing alignment, diagnostic tests and qualification testing described above may be subject to various modification within the scope of the invention. For example, in the described embodiment, the test results and parameters are stored on a disk shipped with the optical module, however certain information, for example, the serial number and test parameter data for a particular optical module could be stored in read only memory (ROM) provided with the module. This information could then be downloaded to the testing computer upon beginning the test procedure. Or the complete test software could be so stored and shipped with the optical module.

In the described embodiment, the test software operates interactively with a user, however completely automatic operation could be achieved with only minor modifications. Instead of instructing the user to cover the module, for example, the program could command a robot arm to place a cover over the module, making the test procedure completely machine implemented. A plurality of test stations could be provided each having an optical module for testing and each under the control of a central computing system for performing the tests simultaneously on the plurality of modules.

In the described embodiment, the software is implemented in the BASIC computer language for use with a personal computer, however any other computer and/or computer language could be used for implementation within the scope of the invention. Likewise, the particular mounting fixture described could be adapted to different optical modules within the scope of the invention. The serial number of a module could be associated with a particular mounting arrangement and/or specific tests and test parameters, so that a test apparatus according to the invention is useful for a collection of optical module varieties.

It will be understood that the above description of the present invention is susceptible to various modifications, changes and adaptations, and the same are intended to be comprehended within the meaning and range of equivalents of the appended claims.

What is claimed is:

1. A computer based method for testing an optical monitoring system which is electrically connected to a computer for exchanging control and data signals therewith, the computer having input means for selecting test commands and display means for displaying screens of information to a user, the method comprising:

displaying on the display means at least one screen showing a plurality of user selectable commands; and performing programmed tests with the computer on the optical monitoring System based on user selected commands input with the input means;

wherein the optical monitoring system includes optical components and electrical circuitry, a light source, a light modifying wheel, a shutter, and a plurality of photodiode arrays having elements, the arrays being disposed at respective stations for receiving light from a respective plurality of optical channels; and wherein the plurality of user selectable commands include a display command, an electrical systems test command, an optical dark test command, a beam alignment test command, a wavelength registration test command, a profile test command, and a filter test command.

2. The method according to claim 1, further comprising:

performing preliminary testing while monitoring the output of the optical monitoring system, the preliminary testing including commanding the optical monitoring system to rotate a light modifying wheel associated therewith to ensure the wheel is responsive, and monitoring the optical monitoring system to check a shutter associated therewith by checking for pulses associated therewith.

3. The method according to claim 1, wherein the photodiode arrays produce output signals and wherein upon selection of a display command, the method further comprises monitoring with the computer the photodiode array output signals from the optical monitoring system, displaying a screen representing the photodiode array output on the computer display means, and selectively varying at least the array represented by the screen, the elements of the arrays represented by the screen, and amplifier gain associated with an array element.

4. The method according to claim 1, wherein upon selection of an electrical systems test command, the method further comprises monitoring the output of the optical monitoring system while selectively performing at least:

an electrical dark test to check the levels of dark current and noise associated with the electrical circuitry of the system;

a digital bit test to check that all bits change state at least once on command in associated digital electrical circuitry of the system;

a shutter speed test to check the rotational speed of the shutter; and a complete light modifying wheel test to test the accuracy of the light modifying wheel.

5. The method according to claim 4, wherein upon selection of an electrical dark test, the method further comprises:

instructing the user to disconnect or turn-off the light source in the optical monitoring system, and to cover the optical monitoring system to block ambient light to the photodiode arrays; and monitoring the output of the optical monitoring system to check levels of dark current and noise associated with the electrical circuitry of the optical monitoring system.

6. The method according to claim 5, wherein the step of monitoring the output of the optical monitoring system comprises:

scanning a photodiode array a predetermined plurality of times;

after each scan in the scanning step, a rolling sum and a rolling standard deviation for each photodiode element is produced;

at the end of the predetermined plurality of scans, producing and comparing an average value for each photodiode element of the photodiode array scanned to minimum and maximum signal level criteria; and determining a standard deviation for each photodiode element and comparing the standard deviations to maximum noise level criteria.

7. The method according to claim 6, wherein the predetermined plurality of scans is 100, the minimum signal level is 0 counts, the maximum signal level is 100 counts, and the maximum noise level is 2.5 counts.

8. The method according to claim 4, wherein the optical monitoring system includes at least a digital to analog converter, an analog to digital converter and an interface, and wherein upon selection of a digital bit test, the method further comprises checking at least the digital to analog converter, the analog to digital converter and the interface for stuck bits by sending and receiving signals to and from the optical monitoring system with the computer to ensure that each bit changes state at least once.

9. The method according to claim 4, wherein upon selection of a shutter speed test, the method further comprises:

polling interrupt signals from the optical monitoring system shutter for a predetermined period of time and keeping a count of the number said interrupt signals received;

dividing the number of interrupts counted by a clock timer of the computer to produce a calculated speed for the shutter; and comparing the calculated speed to predetermined upper and lower acceptable speed values.

10. The method according to claim 4, wherein upon selection of a complete light modifying wheel test, the method further comprises:

commanding the light modifying wheel to move clockwise a predetermined plurality of positions and then back counterclockwise the predetermined plurality of positions;

determining the accuracy of position of the light modifying wheel; and determining whether the light modifying wheel completes each respective move within a predetermined period of time.

11. The method according to claim 4, wherein upon completion of a test of said electrical systems test command which are selectively performed, the method further comprises storing test result data associated with the test performed.

12. The method according to claim 1, wherein upon selection of an optical dark test command, the method further comprises:

monitoring the output of the optical monitoring system with only a track area associated therewith covered to check for ambient light leaking into the optical monitoring system through a cabinet associated with the optical monitoring system.

13. The method according to claim 12, wherein the step of monitoring the output of the optical monitoring system comprises:

scanning a photodiode array a predetermined plurality of times;

after each scan in the scanning step, a rolling sum and a rolling standard deviation for each photodiode element is produced;

at the end of the predetermined plurality of scans, producing and comparing an average value for each photodiode element of the photodiode array scanned to minimum and maximum signal level criteria; and determining a standard deviation for each photodiode element and comparing the standard deviations to maximum noise level criteria.

14. The method according to claim 13, wherein the predetermined plurality of scans is 100, the minimum signal level is 0 counts, the maximum signal level is 100 counts, and the maximum noise level is 2.5 counts.

15. The method according to claim 1, wherein upon selection of a beam alignment test command, the method further comprises monitoring the output of the optical monitoring system to check for cross-talk between optical channels of the optical monitoring system and for proper beam height.

16. The method according to claim 15, wherein checking for cross-talk comprises:

(a) instructing the user to be sure the light source is on and that a track associated with the optical monitoring system is reasonably covered;

(b) measuring dark current for 10 scans with the light modifying wheel in a blocked position;

(c) determining a first average based on the 10 scans for each photodiode element;

(d) instructing the user to place a blocking device in the track at one of a plurality of specified positions, thereby blocking at least one optical channel associated with a respective photodiode array with adjacent channels unobstructed;

(e) setting the signal gain for each photodiode array at a maximum level;

(f) measuring the photodiode current for the respective photodiode element associated with the at least one blocked optical channel for 10 scans with the blocking device at the specified position;

(g) determining a second average based on the 10 scans for each photodiode element;

(h) determining the difference between the first and second averages to thereby determine a cross-talk level;

(i) instructing the user to place the blocking device in the track at another one of the plurality of specified positions;

(j) repeating steps (f) to (i) a predetermined number of times; and (k) comparing determined cross-talk levels with a predetermined acceptable maximum cross-talk.

17. The method according to claim 15, wherein checking for proper beam height comprises:

monitoring the signal from the optical monitoring system;

instructing the user to place a beam height gage in a predetermined position;

monitoring the signal with the beam height gage in place;

comparing the signal without the beam height gage to the signal with the beam height gage to determine a measured difference value; and comparing the measured difference value to a predetermined acceptable difference value.

18. The method according to claim 1, wherein upon selection of a wavelength registration test command, the method further comprises monitoring the output of the optical monitoring system to determine the wavelength mid-frequency and bandwidth of each photodiode array element.

19. The method according to claim 18, wherein the method further comprises:

instructing the user to be sure the light source is on and that a track associated with the optical monitoring system is reasonably covered;

measuring dark current for 10 scans with the light modifying wheel in a blocked position;

determining a first average based on the 10 scans for each photodiode element;

performing a preliminary profile test to ensure that a minimum amount of light can be sensed by each array element;

normalizing the signal from the array by selecting individual gain values for each element so as to balance the signal at a preprogrammed level;

fitting a Gaussian curve to a respective signal detected with each of a plurality of filters in place to find a respective peak signal;

prompting the user to confirm that a peak for a filter position is acceptable;

prompting the user to select one of a plurality of options, the plurality of options including repositioning a filter and repeating the above steps, aborting the wavelength determination process, or continuing;

determining a linear regression using a least squares fit after all filters have been evaluated thereby producing coefficients and residual values of the least squares fit, and calculating a smallest wavelength and a largest wavelength using the coefficients; and comparing the calculated smallest wavelength, the calculated largest wavelength, and the residual values of the least squares fit with predetermined values.

20. The method according to claim 1, wherein upon selection of a profile test command, the method further comprises monitoring the output of the optical monitoring system to measure the amount of light reaching the photodiode array elements and the signal to noise ratio for each optical channel under normal operating conditions.

21. The method according to claim 20, further comprising:
instructing the user to be sure the light source is on and that a track associated with the optical monitoring system is reasonably covered;
measuring dark current for 10 scans with the light modifying wheel in a blocked position;
determining a first average based on the 10 scans for each photodiode element;
setting the gain for each element to a predetermined value for all optical channels;
determining an element number based on each of a plurality of wavelengths to test;
interpolating the signal value for each wavelength from the closest discrete elements corresponding to the desired wavelength;
determining an average of the 10 scans;
comparing the average of the 10 scans with a maximum value and with a minimum value determined using a polynomial based on a typical signal; and
comparing the signal divided by a standard deviation for each element to an optical RMS noise value.
comparing the signal divided by a standard deviation for each element to an optical RMS noise value.

22. The method according to claim 1, wherein upon selection of a filter test command, the method further comprises monitoring the output of the optical monitoring system when different filters are used to test for proper operation.

23. The computer based method according to claim 22, wherein the filter test command tests the optical monitoring system with at least one of a schott glass BG36 filter and a liquid crystal clot simulator used.

24. The method according to claim 22, wherein a schott glass BG36 filter is used and the method further comprises:
instructing the user to be sure the light source is on and that a track associated with the optical monitoring system is reasonably covered;
measuring dark current for 10 scans with the light modifying wheel in a blocked position;
determining a first average based on the 10 scans for each photodiode element;
normalizing the signal from the array by selecting individual gain values for each element so as to balance the signal at a preprogrammed level;
setting the light modifying wheel in the schott glass BG36 filter position; and
determining a peak signal for each of a plurality of wavelengths corresponding to the peak transmittance of the filter by fitting a Gaussian curve to the signal detected around the element expected to show a peak for that wavelength.

25. The method of claim 22, wherein a liquid crystal clot simulator is used and the method further comprises:
instructing the user to be sure the light source is on and that a track associated with the optical monitoring system is reasonably covered;
measuring dark current for 10 scans with the light modifying wheel in a blocked position;
determining a first average based on the 10 scans for each photodiode element;
normalizing the signal from the array by selecting individual gain values for each element so as to balance the signal at a preprogrammed level;
setting the light modifying wheel in the liquid crystal clot simulator position; and
monitoring array output with the liquid crystal clot simulator in position and comparing the output to predetermined expected output values.

26. The computer based method according to claim 2, wherein the plurality of user selectable commands further includes an all tests command, the method further comprising:
upon selection of the all tests command, after performing the preliminary testing, performing the electrical systems test command, the optical dark test command, the beam alignment test command, the wavelength registration test command, the profile test command, and the filter test command automatically.

27. The computer based method according to claim 1, further comprising prompting the user to manually adjust certain portions of the optical monitoring system during performance of the test commands.

28. A computer based method for testing an optical monitoring system which is electrically connected to a computer for exchanging control and data signals therewith, the computer having input means for selecting test commands and display means for displaying screens of information to a user, the method comprising:
displaying on the display means at least one screen showing a plurality of user selectable commands; and
performing programmed tests with the computer on the optical monitoring system based on user selected commands input with the input means;
wherein each optical monitoring system has a unique serial number associated therewith and wherein the method further comprises confirming the programmed tests are suitable for use with the optical monitoring system prior to their execution.

29. A system for testing an optical module of an analytical device having optical components and electrical circuitry, the testing system comprising:
program means comprising program instructions and optical module parameters, for implementing a plurality of tests of at least one optical module;
programmable means comprising a data processing system having processor means for executing the program instructions, storage means for storing program instructions and test data including the optical module parameters, user input means for inputting commands, and display means for displaying screens of information to a user including a menu of available test commands and test results;
interface means for interfacing the optical module to the programmable means to facilitate exchange of control and data signals therewith; and
fixture means for test mounting the optical module during testing and simulating actual operational mounting on the analytical device.

* * * * *

UNITED STATES PATENT AND TRADEMARK OFFICE
CERTIFICATE OF CORRECTION

PATENT NO. : 5,369,484
DATED : November 29, 1994
INVENTOR(S) : Douglas G. Haugen It is certified that error appears in the above-indentified patent and that said Letters Patent is hereby corrected as shown below:

Column 15, claim 1, line 40, delete "System" and replace with -- system --.

Column 19, claim 21, delete lines 38 and 39.

Signed and Sealed this

Eighteenth Day of April, 1995

*Attest:*

BRUCE LEHMAN

*Attesting Officer*   *Commissioner of Patents and Trademarks*